(12) United States Patent
Schwartzbauer et al.

(10) Patent No.: US 11,229,497 B2
(45) Date of Patent: Jan. 25, 2022

(54) ADAPTABLE MEDICAL TRAY

(71) Applicant: EXACTECH, INC., Gainesville, FL (US)

(72) Inventors: Daniel Schwartzbauer, Cranberry Township, PA (US); Randy Schlemmer, Cranberry Township, PA (US)

(73) Assignee: EXACTECH, INC., Gainesville, FL (US)

( * ) Notice: Subject to any disclaimer, the term of this patent is extended or adjusted under 35 U.S.C. 154(b) by 536 days.

(21) Appl. No.: 15/427,702

(22) Filed: Feb. 8, 2017

(65) Prior Publication Data

US 2017/0224434 A1 Aug. 10, 2017

Related U.S. Application Data

(60) Provisional application No. 62/293,138, filed on Feb. 9, 2016.

(51) Int. Cl.
*A61B 50/33* (2016.01)
*A61B 50/20* (2016.01)
(Continued)

(52) U.S. Cl.
CPC .............. *A61B 50/33* (2016.02); *A61B 50/20* (2016.02); *A61B 50/34* (2016.02);
(Continued)

(58) Field of Classification Search
CPC ......... A61B 50/33; A61B 50/20; A61B 50/34; A61B 2050/0005; A61B 2050/0059; A61B 2050/3007; A61B 2050/3009; A61B 2050/3011; A61B 50/3008; A61B 10/00; B65D 85/00; B65D 83/00
(Continued)

(56) References Cited

U.S. PATENT DOCUMENTS 1,084,360 A * 1/1914 Rahm .................. A45C 7/0045
190/108
3,261,307 A * 7/1966 Salkoff ................ A47B 87/002
108/64

(Continued)

FOREIGN PATENT DOCUMENTS

WO 2015174860 A1 11/2015

*Primary Examiner* — J. Gregory Pickett
*Assistant Examiner* — Brijesh V. Patel
(74) *Attorney, Agent, or Firm* — Dinsmore & Shohl LLP

(57) ABSTRACT

Adaptable medical trays are disclosed herein. An adaptable medical tray includes a first component medical tray having a plurality of walls, a bottom, and a removable top, the plurality of walls and the bottom arranged to form a cavity in the first component medical tray; and a second component medical tray removably coupled to the first component medical tray, the second component medical tray including a plurality of walls, a bottom, and a removable top, the plurality of walls and the bottom arranged to form a cavity in the second component medical tray. The first component medical tray and the second component medical tray are constructed of a sterilizable material and the first component medical tray is decouplable from the second component medical tray after a sterilization process without removing the removable tops from the cavities.

20 Claims, 12 Drawing Sheets

(51) Int. Cl.
*A61B 50/34* (2016.01)
*A61B 50/30* (2016.01)
*A61B 50/00* (2016.01)

(52) U.S. Cl.
CPC . *A61B 2050/005* (2016.02); *A61B 2050/0059* (2016.02); *A61B 2050/3007* (2016.02); *A61B 2050/3008* (2016.02); *A61B 2050/3009* (2016.02); *A61B 2050/3011* (2016.02)

(58) Field of Classification Search
USPC ....... 206/370, 373, 503, 508, 504, 439, 140, 206/144, 159; 220/4.27, 23.4, 23.83, 244, 220/250, 323, 553, 833, 297, 529
See application file for complete search history.

(56) References Cited

U.S. PATENT DOCUMENTS

| | | | | |
|---|---|---|---|---|
| 3,307,729 | A * | 3/1967 | Schwartz | B65D 21/0202 220/890 |
| 3,338,452 | A * | 8/1967 | Oakley | H01M 2/0245 220/23.4 |
| 3,603,474 | A * | 9/1971 | Erickson | B65D 1/243 220/23.4 |
| 3,630,344 | A * | 12/1971 | Bergh | A45C 11/34 206/777 |
| 3,805,721 | A * | 4/1974 | Robishaw | B63B 35/38 114/266 |
| 3,823,972 | A * | 7/1974 | Ramer | B65F 1/122 294/68.26 |
| 3,823,973 | A * | 7/1974 | Ramer | B65F 1/122 294/68.26 |
| 3,851,936 | A * | 12/1974 | Muller | A47B 87/02 312/108 |
| 3,872,555 | A * | 3/1975 | Link | B65D 90/0013 24/590.1 |
| 3,938,461 | A * | 2/1976 | Marriner | B63B 35/70 114/249 |
| 4,026,615 | A * | 5/1977 | Tazaki | G11B 23/023 206/387.1 |
| 4,165,908 | A * | 8/1979 | Cooper | A47B 87/02 108/64 |
| 4,212,251 | A * | 7/1980 | DiMartino | B65D 90/0013 220/1.5 |
| 4,523,680 | A * | 6/1985 | Saito | G11B 23/023 206/387.15 |
| 4,619,363 | A * | 10/1986 | Wolfseder | B65D 21/0224 206/372 |
| 4,695,184 | A * | 9/1987 | Robishaw | B60P 7/13 220/23.4 |
| 4,741,449 | A * | 5/1988 | Bersani | B65D 90/0013 220/1.5 |
| 4,819,820 | A * | 4/1989 | Weiner | B65D 88/022 220/1.5 |
| 4,844,565 | A * | 7/1989 | Brafford | A47B 87/008 312/107.5 |
| 4,886,239 | A * | 12/1989 | Stimmel | F25C 1/243 249/117 |
| 4,889,254 | A * | 12/1989 | Vola | A45C 7/0045 220/23.4 |
| 5,050,755 | A * | 9/1991 | Strawder | B65D 21/0202 220/23.4 |
| 5,263,576 | A * | 11/1993 | Boreen | B65D 43/20 206/455 |
| 5,325,975 | A * | 7/1994 | Brown | A47B 87/0292 211/189 |
| 5,381,916 | A * | 1/1995 | Strawder | B65D 21/0202 220/212 |
| 5,394,983 | A * | 3/1995 | Latulippe | A61L 2/26 206/370 |
| 5,441,707 | A * | 8/1995 | Lewis | A61L 2/06 422/300 |
| 5,540,901 | A | 7/1996 | Riley | |
| 5,577,629 | A * | 11/1996 | Rosler | B25H 3/023 220/345.3 |
| 5,671,856 | A * | 9/1997 | Lisch | A01K 97/06 206/519 |
| 5,890,613 | A * | 4/1999 | Williams | A45C 7/0045 220/23.4 |
| 6,012,577 | A | 1/2000 | Lewis et al. | |
| 6,059,135 | A * | 5/2000 | James | B65D 55/145 220/23.4 |
| 6,073,737 | A * | 6/2000 | Kang | A45C 5/14 |
| 6,073,790 | A * | 6/2000 | Umiker | B65D 11/1833 220/315 |
| 6,371,321 | B1* | 4/2002 | Lee | B65D 21/0204 220/23.4 |
| 7,322,477 | B2* | 1/2008 | Schweitz | A63B 60/58 206/579 |
| 7,428,973 | B2* | 9/2008 | Barth | B65D 11/1833 220/7 |
| 7,481,316 | B2* | 1/2009 | Huruta | B65D 21/0204 206/506 |
| 7,748,529 | B2* | 7/2010 | Foreman | A61L 2/26 206/370 |
| 7,780,026 | B1* | 8/2010 | Zuckerman | A61L 2/26 206/370 |
| 7,905,353 | B2* | 3/2011 | Baker | B65D 1/28 206/370 |
| 7,909,191 | B2 | 3/2011 | Baker et al. | |
| 9,198,811 | B2 | 12/2015 | Pizzato et al. | |
| 9,314,076 | B2* | 4/2016 | Edme | A45C 5/14 |
| 9,327,890 | B1* | 5/2016 | Connelly | B65D 71/70 |
| 9,364,088 | B2 | 6/2016 | Abene | |
| 9,414,893 | B2* | 8/2016 | Jacobson | B65D 81/127 |
| 9,566,990 | B2* | 2/2017 | Bar-Erez | A47B 47/00 |
| 2002/0079313 | A1* | 6/2002 | Grayson | A01K 97/06 220/23.4 |
| 2004/0129595 | A1* | 7/2004 | Dane | A61L 2/26 206/503 |
| 2005/0033430 | A1* | 2/2005 | Powers | A61B 17/7059 623/17.11 |
| 2006/0091030 | A1* | 5/2006 | Tawanapoor | A47G 19/24 206/320 |
| 2007/0215507 | A1* | 9/2007 | Glenn | A61B 50/33 206/438 |
| 2012/0211492 | A1* | 8/2012 | Kelly | B65D 5/302 220/265 |
| 2013/0161320 | A1* | 6/2013 | Myers | B65D 21/0204 220/23.4 |
| 2014/0083886 | A1 | 3/2014 | Winterrowd et al. | |
| 2015/0151017 | A1 | 6/2015 | Tipton et al. | |
| 2016/0059987 | A1* | 3/2016 | Keast | E21B 25/005 206/562 |
| 2016/0251115 | A1* | 9/2016 | Barry | B25H 3/006 220/23.4 |

* cited by examiner

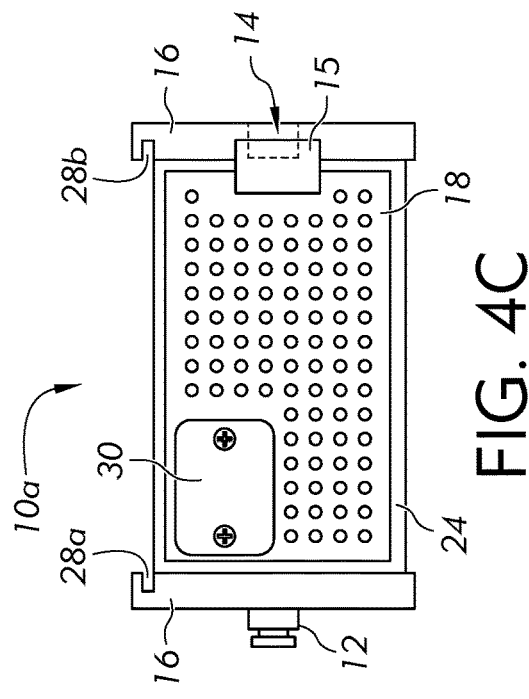
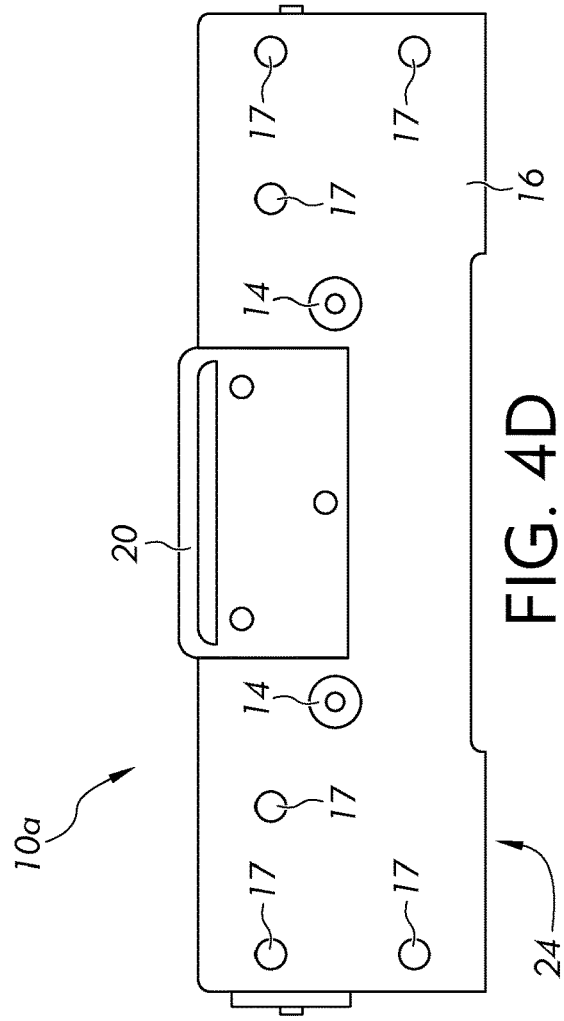
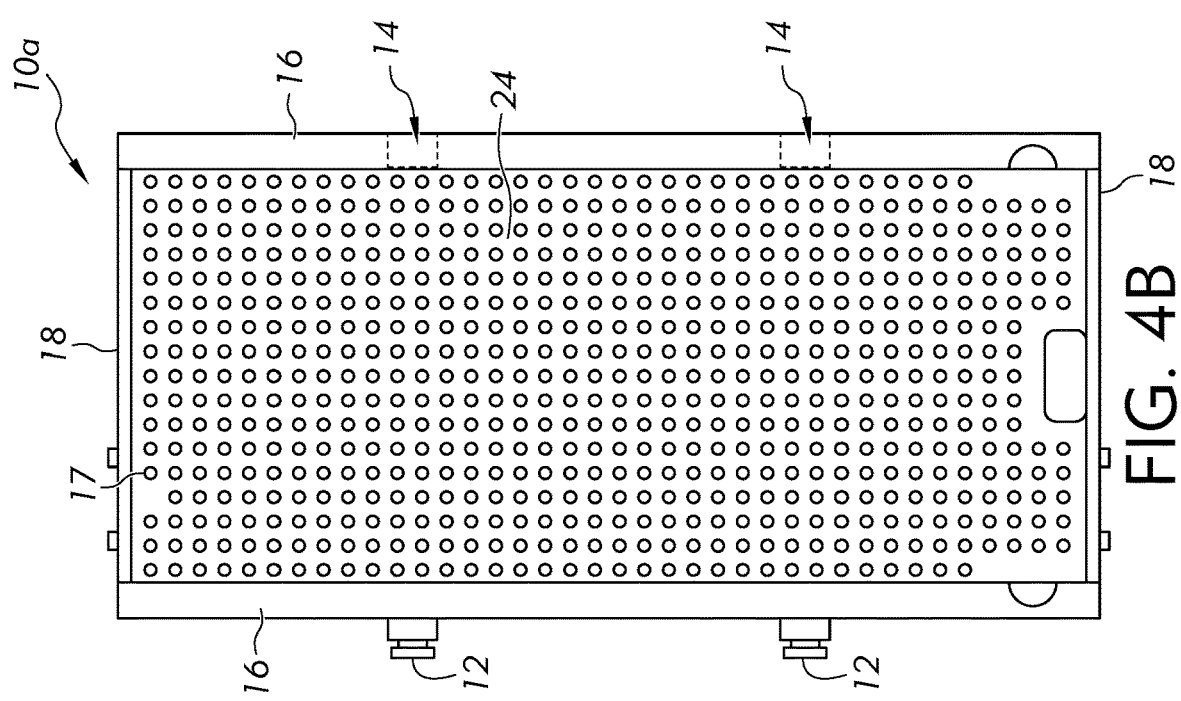

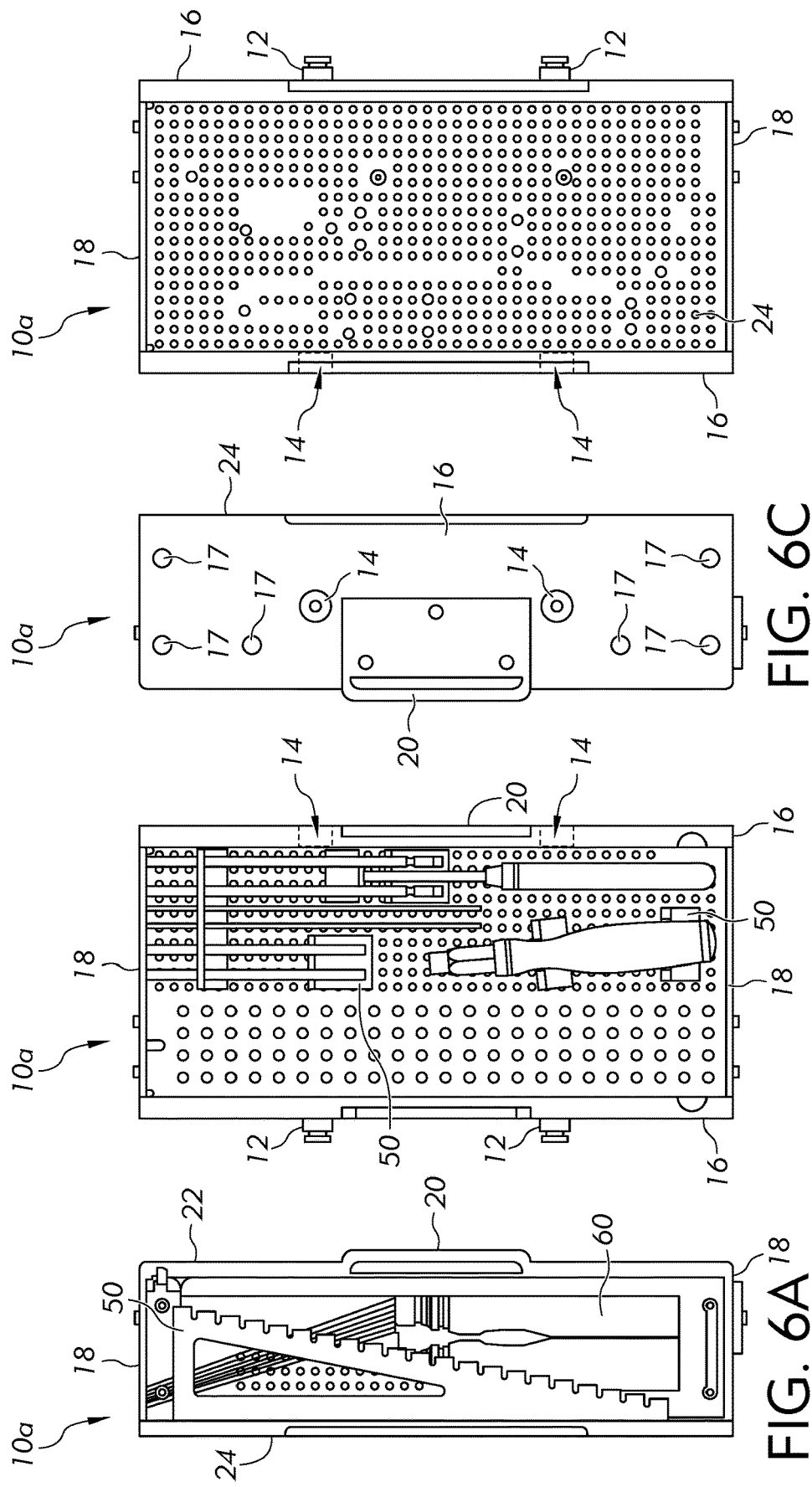

ADAPTABLE MEDICAL TRAY

CROSS-REFERENCE TO RELATED APPLICATION

The present application claims priority to U.S. Provisional Patent Application Ser. No. 62/293,138, filed Feb. 9, 2016 and entitled "Adaptable Medical Tray," the entire contents of which is incorporated herein by reference.

TECHNICAL FIELD

The present specification generally relates to apparatuses, systems, and methods for holding medical equipment and, more specifically, to a plurality of attached medical trays that contain specific stock keeping units (SKUs) and are separable from one another after undergoing a sterilization process.

BACKGROUND

Medical trays that are used to store and transport medical equipment generally include cases, caddies, containers, or the like that are stocked with a large number of medical equipment pieces so as to ensure that medical personnel have access to everything that may be needed during a particular procedure. Because of the large number of medical procedures and because of particular preferences of medical personnel, the number of medical equipment pieces that must be included in a particular medical tray has become unwieldy. In addition, a majority of the medical equipment pieces go unused in a particular medical procedure, which means such pieces cannot be used for other procedures occurring at substantially the same time, must be discarded, or must be re-sterilized before they can be used for subsequent procedures. As a result, personnel at a hospital, a doctor's office, a surgical center, and/or the like, as well as a medical device sales technician and/or the like must maintain large inventories of the medical trays to ensure that the necessary equipment is available for each medical procedure that occurs at a given time. Such large inventories are expensive to maintain, require excessive manpower, cannot be used to quickly react to issues that may arise (such as instances when a new medical tray is needed due to a medical device falling on the floor, a sterile tray opening outside of a sterile field, and/or the like), can cause canceled or postponed procedures, and/or the like.

Some customizable trays may allow medical personnel to construct their own specialized kits that contain the precise medical equipment needed for a particular procedure. However, such solutions require medical personnel to assemble the specialized kits on their own, sterilize the kits, and conduct other preparation tasks that are time consuming and inconvenient. Other attempted solutions have resulted in modular trays that can be coupled together such that customized kits can be created based on the medical equipment that is needed for a particular procedure. However, such customized kits still tend to contain an excessive amount of instrumentation and/or the like that ultimately is unused for a particular procedure. Moreover, such customized kits are particularly configured such that the modular trays cannot be separated from each other once they have been sterilized.

Accordingly, a need exists for an adaptable medical tray that incorporates a plurality of component medical trays, each of which contains specific medical equipment that has been customized for a particular procedure and/or according to particular medical personnel demands, can be coupled to other component medical trays, and is separable from other component medical trays after a sterilization process without requiring a top, lid, or the like to be removed.

SUMMARY

In one embodiment, an adaptable medical tray includes a first component medical tray having a first plurality of walls, a first bottom, and a first removable top, the first plurality of walls and the first bottom arranged to form a first cavity in the first component medical tray. The adaptable medical tray further includes a second component medical tray removably coupled to the first component medical tray, the second component medical tray including a second plurality of walls, a second bottom, and a second removable top, the second plurality of walls and the second bottom arranged to form a second cavity in the second component medical tray. The first component medical tray and the second component medical tray are constructed of a sterilizable material and the first component medical tray is decouplable from the second component medical tray after a sterilization process without removing the first removable top from the first cavity and without removing the second removable top from the second cavity.

In another embodiment, an adaptable medical tray includes a first component medical tray having a first plurality of side walls, a first plurality of end walls, a first bottom, and a first removable top. The first plurality of side walls, the first plurality of end walls, and the first bottom arranged to form a first cavity in the first component medical tray. The adaptable medical tray further includes a second component medical tray comprising a second plurality of side walls, a second plurality of end walls, a second bottom, and a second removable top. The second plurality of side walls, the second plurality of end walls, and the second bottom arranged to form a second cavity in the second component medical tray. At least one of the first plurality of side walls comprises at least one male mating feature and at least one of the second plurality of side walls comprises at least one female mating feature that corresponds to the at least one male mating feature such that when the at least one male mating feature is inserted in the at least one female mating feature, the first component medical tray is removably coupled to the second component medical tray. The first component medical tray and the second component medical tray are constructed of a sterilizable material and the first component medical tray is decouplable from the second component medical tray after a sterilization process without removing the first removable top from the first cavity and without removing the second removable top from the second cavity.

In yet another embodiment, an adaptable medical tray includes a first component medical tray constructed of a sterilizable material and having a cavity formed by a first side wall having a plurality of male mating features, a second side wall having a plurality of female mating features, a plurality of end walls, a bottom, and a removable top. The adaptable medical tray further includes a second component medical tray constructed of a sterilizable material and having a cavity formed by a first side wall having a plurality of male mating features, a second side wall having a plurality of female mating features, a plurality of end walls, a bottom, and a removable top. The adaptable medical tray further includes a third component medical tray constructed of a sterilizable material and having a cavity formed by a first side wall having a plurality of male mating features, a second side wall having a plurality of female mating features, a plurality of end walls, a bottom, and a removable top. The first component medical tray is removably coupled to the second component medical tray and the third component medical tray via the male mating features of the first side wall of the first component tray and the female mating features of the second side wall of the first component tray. The first component medical tray is decouplable from the second component medical tray and the third component medical tray after a sterilization process without removing the removable top from the first cavity, the removable top from the second cavity, and the removable top from the third cavity.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 4B depicts a detailed bottom plan view of an illustrative component medical tray with a lid according to one or more embodiments shown and described herein;

FIG. 4C depicts an end view of an illustrative component medical tray according to one or more embodiments shown and described herein;

FIG. 4D depicts a side view of an illustrative component medical tray according to one or more embodiments shown and described herein;

FIG. 6A depicts a side cutaway view of an illustrative component medical tray including a retention bracket according to one or more embodiments shown and described herein;

FIG. 6B depicts a top plan view of an illustrative component medical tray including a screw caddy and driver components according to one or more embodiments shown and described herein;

FIG. 6C depicts a side view of the component medical tray of FIG. 6B according to one or more embodiments shown and described herein;

FIG. 6D depicts a bottom view of an illustrative component medical tray including a screw caddy extending along an entire interior of the component medical tray according to one or more embodiments shown and described herein;

DETAILED DESCRIPTION

Figure 1:
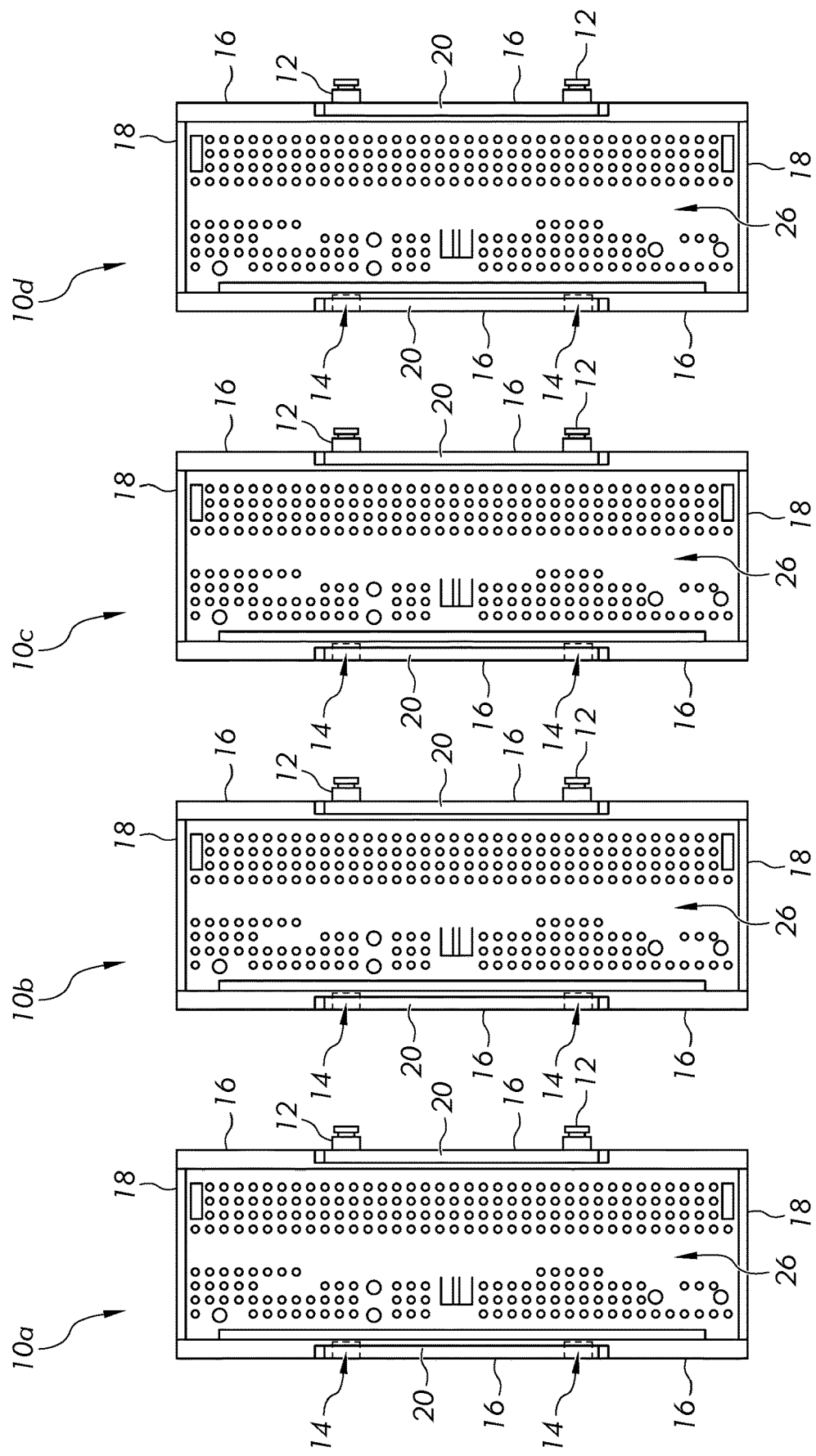
FIG. 1 depicts a top plan view of a plurality of illustrative component medical trays without lids and in a decoupled configuration according to one or more embodiments shown and described herein.

The embodiments described herein are generally directed to a plurality of component medical trays that can be coupled in any number of configurations to form an adaptable medical tray. Each component medical tray may be an apparatus that contains one or more pieces of medical equipment. As such, the adaptable medical tray can be specifically formed by joining particular component medical trays without any tools or additional components. The component medical trays may contain particular medical equipment that may be needed for a particular procedure, and can easily be arranged according to the preferences of certain medical personnel, and/or the like. As a result, the adaptable medical tray can easily be configured to only contain medical equipment that is to be used by particular medical personnel for a particular procedure, thereby avoiding providing excess medical equipment that will go unused during a particular procedure, by particular medical personnel, and/or the like. Moreover, the adaptable medical tray can be easily split into its component medical trays after sterilization without removing respective tops from the component medical trays such that the component medical trays can be transported to different locations, can be swapped out, and/or the like. While the present disclosure specifically describes splitting the adaptable medical tray into its component medical trays after a sterilization process, it should be understood that this is merely illustrative. Accordingly, it should be understood that the adaptable medical tray may also be split into its component medical trays prior to a sterilization process without departing from the scope of the present disclosure.

As used herein, "medical equipment" generally relates to any tools, implements, instruments, implants, appliances, devices and/or the like that may be used in the medical field. For example, medical equipment may include surgical tools such as drills, bits, countersinks, drivers, guide wires, depth gauges, handles, staple drill guides, and the like. In another example, medical equipment may also include components, devices, or the like that may be retained within a subject's body after a procedure, such as screws, staples, suture material, implants, and the like. Medical equipment may also include other components not specifically described herein. Because certain medical equipment may come in contact with an inside of a subject's body, it may be necessary to ensure that such medical equipment is appropriately sterilized to avoid complications such as infections or the like.

As used herein, "sterilizable" generally refers to a property of a material that can withstand a sterilization process. More specifically, a sterilizable material may be any material that is able to withstand certain temperatures, pressures, or the like of a sterilization device such as an autoclave. In addition, a sterilizable material may be a material that can be exposed to water, steam, or the like. Heat-labile materials (such as some plastics) are not sterilizable because they may melt. Paper, paper-based products, and/or the like that may be damaged by steam may also not be suitable as a sterilizable material. While any sterilizable material may be used herein, certain particular materials are described in greater detail hereinbelow.

As used herein, a "sterilization process" refers to a process that causes the destruction and/or irreversible inactivation of all microorganisms on any material placed within sterilizing chamber. For example, a sterilizable material may be placed in a sterilizing device, such as an autoclave, and exposed to an environment sufficiently kills any bacteria, viruses, molds, spores, prions, and/or the like that may be present on the material. More specifically, a sterilizable material may be placed in an autoclave and subjected to high-pressure saturated steam at a high temperature (e.g., about 121° C., about 134° C., and/or the like) for a period of time (e.g., about 15 minutes, about 20 minutes, about 30 minutes, about 1 hour, about 2 hours, or the like). An illustrative example of high-pressure saturated steam may be steam that is provided at a pressure of about 100 kilopascals (kPa). However, other pressures should generally be understood. In some embodiments, a device placed in the autoclave may be marked with a chemical indicator or the like (e.g., autoclave tape) that contain a dye that is only activated when a certain amount of heat, steam, pressure, and/or the like is maintained for a particular period of time.

It should further be understood that, once sterilized materials are removed from an autoclave, they must remain within a sterile environment, such as a sterile laboratory, a sterile vacuum hood, a sterile transport bag/wrap, and/or the like to avoid contamination. Contamination may occur if such sterilized materials are removed from the sterile environment such that microorganisms can attach and/or grow on the surface thereof. As such, a decoupling of the various components (as described in greater detail herein) may occur in a sterile environment to avoid contamination.

Medical trays that are used to store and transport medical equipment enjoy widespread use in the medical device and instrumentation industries. Such trays include, but are not limited to, cases, caddies, containers, or the like that are used for compiling, storing, and transporting stockkeeping units ("SKU") or kits of components that make up a product portfolio or particular set of medical components provided by a company such as a medical equipment manufacturer, a medical supply company, and/or the like. The trays combine the SKUs into a single module that may be transported by a sales associate, medical personnel, or the like to procedures that are performed by other medical personnel, such as doctors, surgeons, assistants, nurses, or the like.

The medical trays are typically designed so the compiled SKUs can be sterilized in one unit preceding a procedure. The contents are defined with a certain combination of SKUs. The SKUs can also be grouped into SKU families, which are typically a number of SKUs that have been submitted and cleared by the Food and Drug Administration ("FDA") under a certain approval or a 510 (k) number. Surgeons may use the SKUs and SKU families to treat a subject under a preferred treatment method based on the subject's disease in accordance with a surgical algorithm of care ("SAOC").

Medical device sales technicians transport, carry and store bulky medical trays including various combinations of SKUs and SKU families to places where a medical procedure occurs. The trays with the full SKUs and SKU families may include sizes for nearly all potential situations that a medical professional may encounter during the procedure, including sizes of implants and instruments that are not required during each procedure. The medical device sales technician frequently is aware of a subset of the SKUs and SKU families that are required for a procedure, but must transport, carry, and store full medical trays with numerous implants, instruments, and parts that are not necessary for the specific procedure because the trays have an over-inclusive amount of implants, instruments and parts. The over-inclusion of medical components in the SKUs and SKU families has been referred to as a "SKU proliferation epidemic" that continues to escalate in order to provide as many options as possible for particular medical personnel and/or particular medical procedures.

Delivery of the SKUs and SKU families to an end user such as medical personnel is provided in a relatively large tray or combination of trays. These individual trays either contain an SKU family, such as, for example, a cannulated screw system, multiple SKU families, or a combination of SKU family segments. The quantity of SKUs in each tray varies depending on the intended use of each tray's contents, but the trays inevitably contain a significant amount more SKUs than needed for each procedure in order to accommodate situations that do not arise in each procedure.

Certain medical trays may include separable parts, such as, for example, trays that have inserts that can be removed. Inserts within trays cannot be removed after sterilization because the lid of the medical tray would necessarily have to be removed from the tray in order to remove the insert and the insert would not otherwise include any protection or ability to hold components for transport. As such, the inserts cannot readily be separated from the trays after a sterilization procedure to deliver to various medical personnel. Therefore, medical device sales technicians or the like must carry an excessive amount of medical equipment to each end user, where a certain amount of the medical equipment goes unused.

Other medical trays may include a plurality of individual trays that can be coupled together. However, such trays (or components therein) may be difficult to join or separate. For example, such trays cannot be adequately be separated after a sterilization process without potentially exposing the components held therein. This is because such trays include a single lid/top piece that spans all of the coupled medical trays and restricts decoupling of the trays after the sterilization procedure. Removal of such a lid/top piece would expose the components held therein, thereby potentially causing components to spill out of the containers. Moreover, such trays typically require additional extra pieces, such as clips, support trays, and/or the like to maintain a connectedness between component trays. Such additional pieces add to the cost of manufacture, can become lost or detached during transport, may be difficult to install or require additional installation steps, and/or the like. In addition, such additional pieces may require use of tools, such as drivers, riveters, or the like to join the component trays together and/or separate the component trays. Such tools may be inconvenient to use, may not be readily available, and/or the like. As such, the trays cannot readily be separated either before or after a sterilization procedure. Particularly, such trays cannot be separated after a sterilization procedure to deliver to various medical personnel. As mentioned above, medical device sales technicians or the like must still carry an excessive amount of medical equipment to each end user, where a certain amount of the medical equipment goes unused.

The combination of the industry's need to provide as many options as possible (SKU proliferation epidemic) and the industry's current practice of filling the tray with (or coupling multiple trays having) SKU families, multiple SKU families or a combination of SKU family segments has created significant amounts of on-hand inventory. More specifically, the breaking of SKUs, SKU families, and multiple SKU families into a plurality of different trays/combinations to suit specific options, SAOCs, and/or the like has resulted in increased inventory issues whereby a large number of trays must be maintained at all times. This current practice also creates complex field logistics, as a majority of SKUs contained in a tray are typically not used during every surgery and sit idle while deployed into the field. The large amount of extra equipment creates substantial field inventory inefficiencies. Both excessive on-hand inventory and substantial field inventory inefficiencies are exposing the industry to substantial unnecessary costs.

Figure 2:
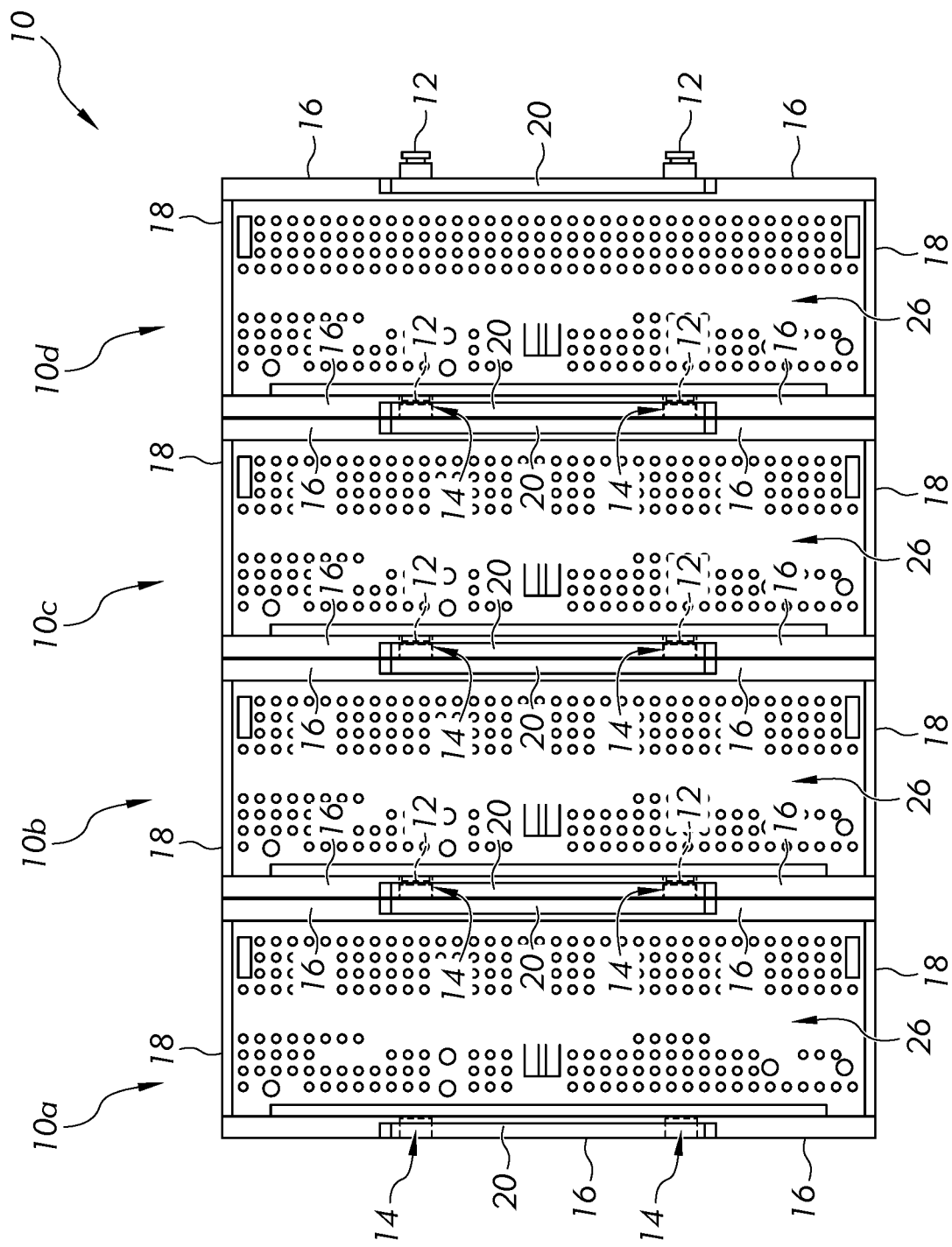
FIG. 2 depicts a top plan view of a plurality of illustrative component medical trays without lids and in a coupled configuration to form an illustrative adaptable medical tray according to one or more embodiments shown and described herein.
Figure 11:
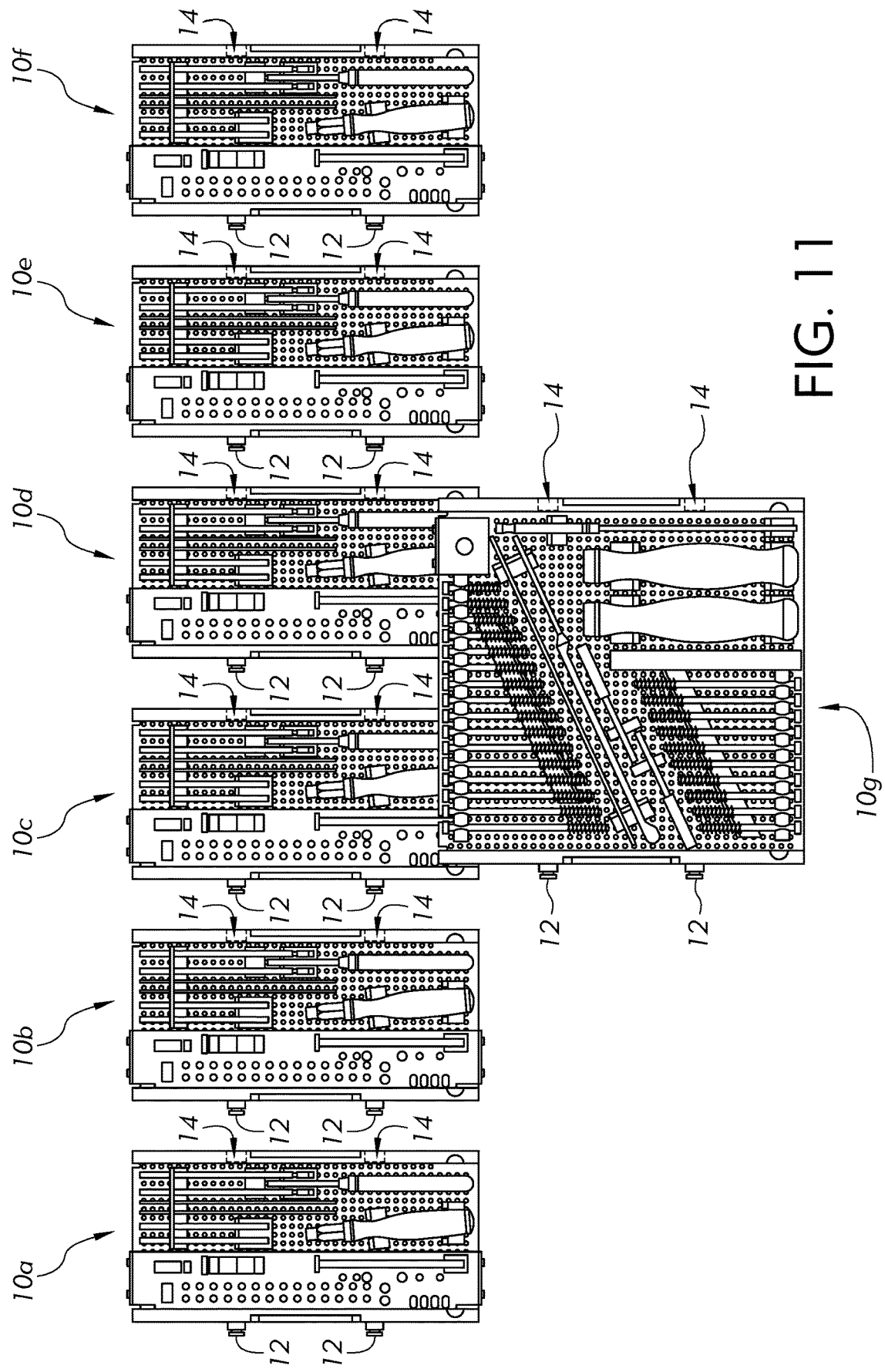
FIG. 11 depicts a top plan view of a plurality of different illustrative component medical trays arranged in a decoupled configuration according to one or more embodiments shown and described herein.
Figure 12:
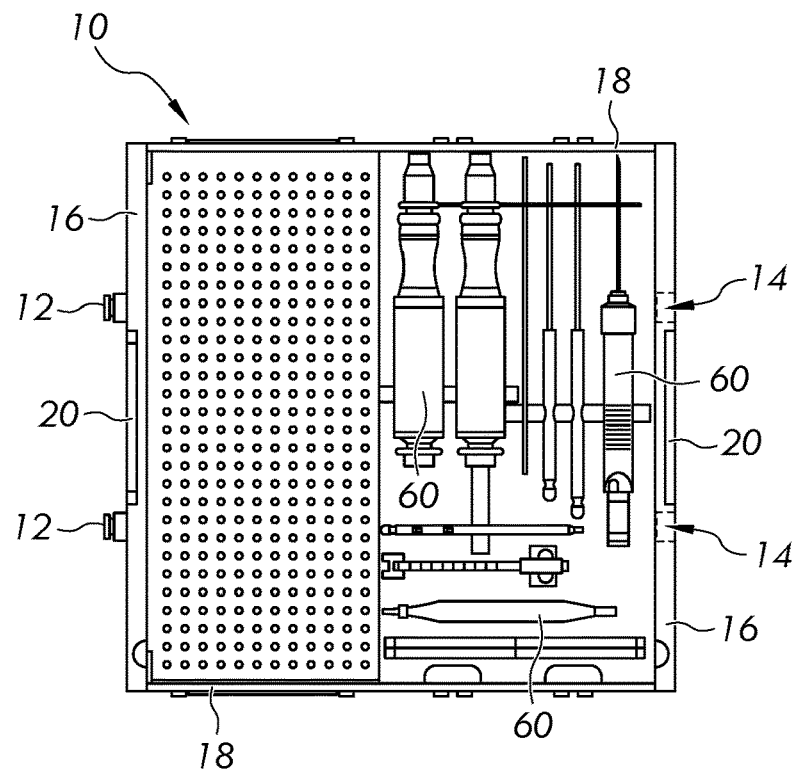
FIG. 12 depicts a top plan view of an illustrative component medical tray with removed tray inserts according to one or more embodiments shown and described herein.
Figure 13A:
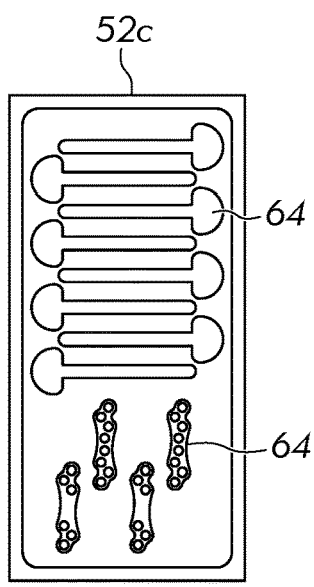
FIG. 13A depicts a top plan view of an illustrative tray insert that may be inserted into a component medical tray according to one or more embodiments shown and described herein.
Figure 13B:
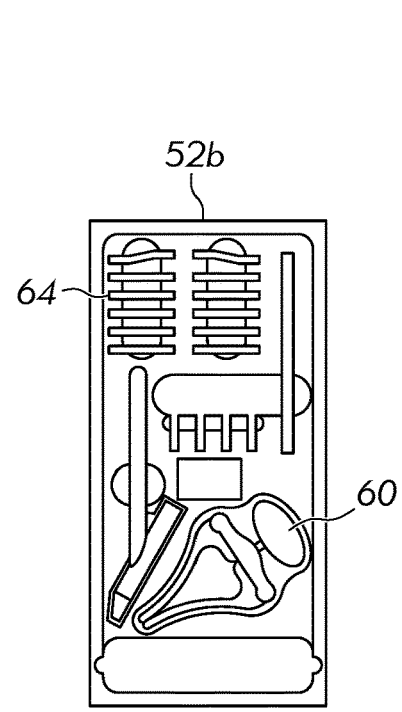
FIG. 13B depicts a top plan view of another illustrative tray insert that may be inserted into a component medical tray according to one or more embodiments shown and described herein.
Figure 13C:
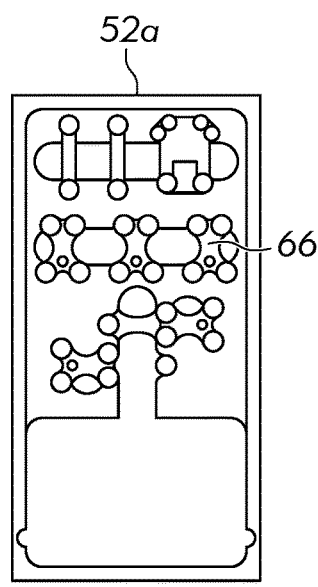
FIG. 13C depicts a top plan view of yet another illustrative tray insert that may be inserted into a component medical tray according to one or more embodiments shown and described herein.

FIGS. 1 and 2 depict an adaptable medical tray, generally designated 10, that includes a plurality of component medical trays 10a, 10b, 10c, 10d. The component medical trays 10a, 10b, 10c, 10d are shown in a decoupled configuration in FIG. 1 and in a coupled configuration in FIG. 2. As shown in FIG. 2, the component medical trays 10a, 10b, 10c, 10d may be coupled together to form the adaptable medical tray 10. While FIG. 2 depicts the component medical trays 10a, 10b, 10c, 10d as being coupled in a particular order, the arrangement of the component medical trays 10a, 10b, 10c, 10d is not limited by this disclosure. That is, the adaptable medical tray 10 may include the component medical trays 10a, 10b, 10c, 10d arranged in a different manner, including a different side-by-side arrangement, a stacked arrangement, and/or the like. While four (4) component medical trays 10a, 10b, 10c, 10d are shown in FIGS. 1 and 2, it should be understood that the adaptable medical tray 10 is not limited to such a specific number. For example, the adaptable medical tray 10 may include one (1) component medical tray, two (2) component medical trays, three (3) component medical trays, five (5) component medical trays, or greater. In some embodiments, as particularly shown in FIG. 11, the adaptable medical tray 10 may include seven (7) component medical trays 10a, 10b, 10c, 10d, 10e, 10f, 10g. In some embodiments, the number of component medical trays may be such that the adaptable medical tray 10 is suitably shaped and sized for carrying, storing, and transporting the adaptable medical tray 10 for medical procedures. In some embodiments, the number of component medical trays may be such that the adaptable medical tray 10 contains all necessary medical components for a particular procedure, a sufficient number of medical components for a particular operator's preferences, a sufficient number of medical components to comply with certain medical guidelines, and/or the like.

The adaptable medical tray 10 may allow for creation and building of various sized trays, using various combinations of the component medical trays 10a, 10b, 10c, 10d. For example, the component medical trays 10a, 10b, 10c, 10d, may be independently assembled into modules that can "stand alone" as the adaptable medical tray 10 or can be coupled/decoupled with any other component medical trays 10a, 10b, 10c, 10d to form the adaptable medical tray 10. Any of the component medical trays 10a, 10b, 10c, 10d can be coupled to any other of the component medical trays 10a, 10b, 10c, 10d to construct an adaptable medical tray 10 containing any combination of SKUs, SKU families, SKU family segments, and/or the like. The modular capability of the component medical trays 10a, 10b, 10c, 10d may provide an option to couple the various component medical trays 10a, 10b, 10c, 10d based on customized facility need, patient disease, SAOC, and/or the like, and create logistical convenience, establish field inventory efficiency, reduce on-hand inventory, and/or the like. Moreover, the modular capability of the component medical trays 10a, 10b, 10c, 10d may further provide the option to adjust the contents of the adaptable medical tray 10 on the fly to adjust to last minute changes in procedures, medical personnel preferences, to replace equipment that may have become contaminated, and/or the like. Because each component medical tray 10a, 10b, 10c, 10d is separable from the other component medical trays 10a, 10b, 10c, 10d, such adjustments can be completed without the need to re-sterilize equipment.

In various embodiments, each of the component medical trays 10a, 10b, 10c, 10d, may include a plurality of walls, such as, for example, a plurality of side walls 16 and/or a plurality of end walls 18. That is, a first component medical tray 10a may include a first plurality of side walls 16 and/or a first plurality of end walls 18, a second component medical tray 10b may include a second plurality of side walls 16 and/or a second plurality of end walls 18, a third component medical tray 10c may include a third plurality of side walls 16 and/or a third plurality of end walls 18, and the like.

Figure 3:
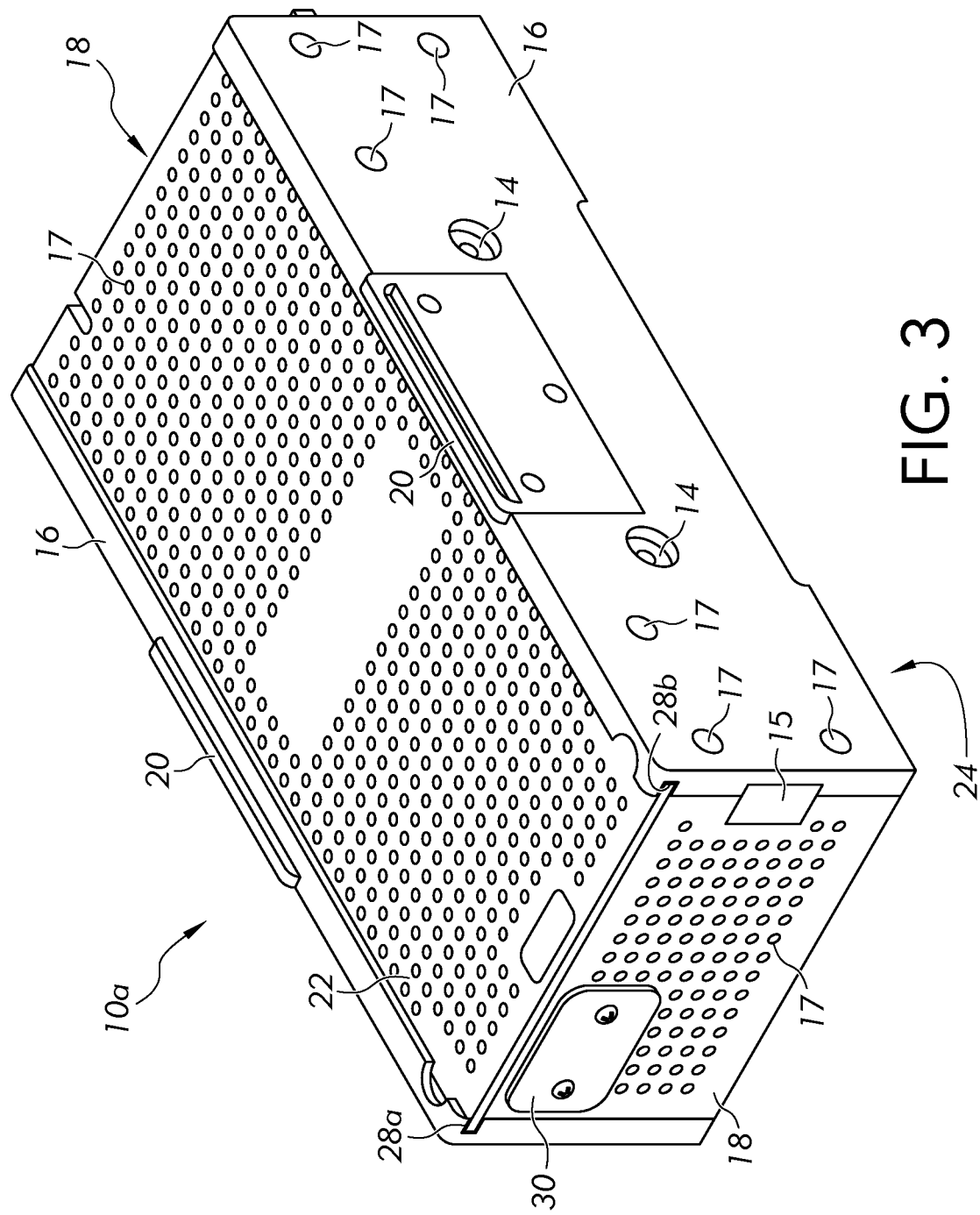
FIG. 3 depicts a top perspective view of an illustrative component medical tray with a lid according to one or more embodiments shown and described herein.

Referring also to FIGS. 3 and 4B, a component medical tray 10a may include a removable top 22 and a bottom 24 in addition to the plurality of walls. That is, a first component medical tray 10a may include a first removable top 22 and/or a first bottom 24, a second component medical tray 10b may include a second removable top 22 and/or a second bottom 24, a third component medical tray 10c may include a third removable top 22 and/or a third bottom 24, and the like. For purposes of brevity, the various side walls 16, end walls 18, removable tops 22, and bottoms 24 will be discussed with respect to a single component medical tray 10a, but it should be understood that the following description applies to all component medical trays described herein.

As shown in FIGS. 1-4D, the side walls 16, the end walls 18, and the bottom 24 may be arranged to form a cavity 26 in the component medical tray 10a. That is, the bottom 24 may be coupled to each of the side walls 16 and the end walls 18 to form the cavity 26, where the side walls 16, the end walls 18, and the bottom 24 define boundaries for the cavity 26. For example, the bottom 24 may be positioned such that each of a plurality of edges of the bottom 24 is coupled to a side wall 16 or an end wall 18. In addition, an edge of each side wall 16 (e.g., an edge that is perpendicular to the edge coupled to the bottom 24) may be coupled to an edge of each end wall 18. In some embodiments, one or more of the end walls 18 may be pivotably secured to one of the side walls 16 such that the end walls 18 may be pivoted from a closed position to an open position to gain access to various medical equipment that may be contained within the component medical tray 10a. In other embodiments, various portions of the component medical tray 10a may be formed in a single piece construction. That is, the side walls 16, the end walls 18, and the bottom 24 may be formed as a single component with the side walls 16 and the end walls 18 extending from the bottom 24.

The removable top 22 may be particularly constructed and/or configured such that it can be removed from the component medical tray 10a. For example, it may be necessary to remove the removable top 22 to access the cavity 26 such that medical equipment can be placed within the cavity 26 or removed from the cavity 26. In some embodiments, the removable top 22 may be slidably removed from the component medical tray. That is, as specifically shown in FIG. 3, the side walls 16 may include slots 28a, 28b therein for receiving the removable top 22 and allowing the removable top 22 to slide along a length of the side walls 16. In other embodiments, the removable top 22 may be pivotally coupled to one or more of the side walls 16 and the end walls 18 such that the removable top 22 can swivel between a closed configuration and an open configuration for access to the cavity 26. In some embodiments, the removable top 22 may be retained in a coupled configuration by a latch or the like to ensure that the removable top 22 is not inadvertently removed, does not accidentally slide off, does not accidentally swing open, or the like. The latch is not limited by this disclosure, and may generally be any device that can selectively maintain the coupled configuration of the removable top 22 to the component medical tray 10a.

While the component medical tray 10a may have an openable and closeable top 22 and/or openable/closable end walls 18, the present disclosure is not limited to such. However, in some embodiments, such configurations may be desirable for the convenience of a user to gain access to the cavity 26 of the component medical tray 10a.

In various embodiments, the component medical trays 10a, 10b, 10c, 10d may each include one or more mating features, retention pieces, and/or the like for removably coupling the component medical trays 10a, 10b, 10c, 10d to each other, such that a pair of component medical trays are coupled along a common interface. In some embodiments, the mating features may be integrated within the component medical trays 10 a, 10 b, 10 c, 10 d so as to avoid the need for external coupling devices (e.g., clips, screws, combined lids, holding trays, and/or the like). Moreover, such mating features may be integrated within the component medical trays 10a, 10b, 10c, 10d so as to provide a toolless means of coupling the various component medical trays together 10a, 10b, 10c, 10d. That is, no tools or the like must be located or used to couple (or decouple) the component medical trays 10a, 10b, 10c, 10d.

To ensure a plurality of different arrangements of the coupling of the component medical trays 10a, 10b, 10c, 10d, each of the component medical trays may include a plurality of different features. For example, in some embodiments, each one of the component medical trays 10a, 10b, 10c, 10d may include at least one male mating feature 12 and at least one female mating feature 14. In some embodiments, the at least one male mating feature 12 and the at least one female mating feature 14 may be disposed on opposing side surfaces. For example, the at least one male mating feature 12 may be disposed on a first one of the side walls 16 and the at least one female mating feature 14 may be disposed on a second one of the side walls 16. The at least one male mating feature 12 and the at least one female mating feature 14 may be outwardly disposed such that they are not located on an inside surface of the respective side walls (e.g., a surface that faces the cavity 26).

Figure 4A:
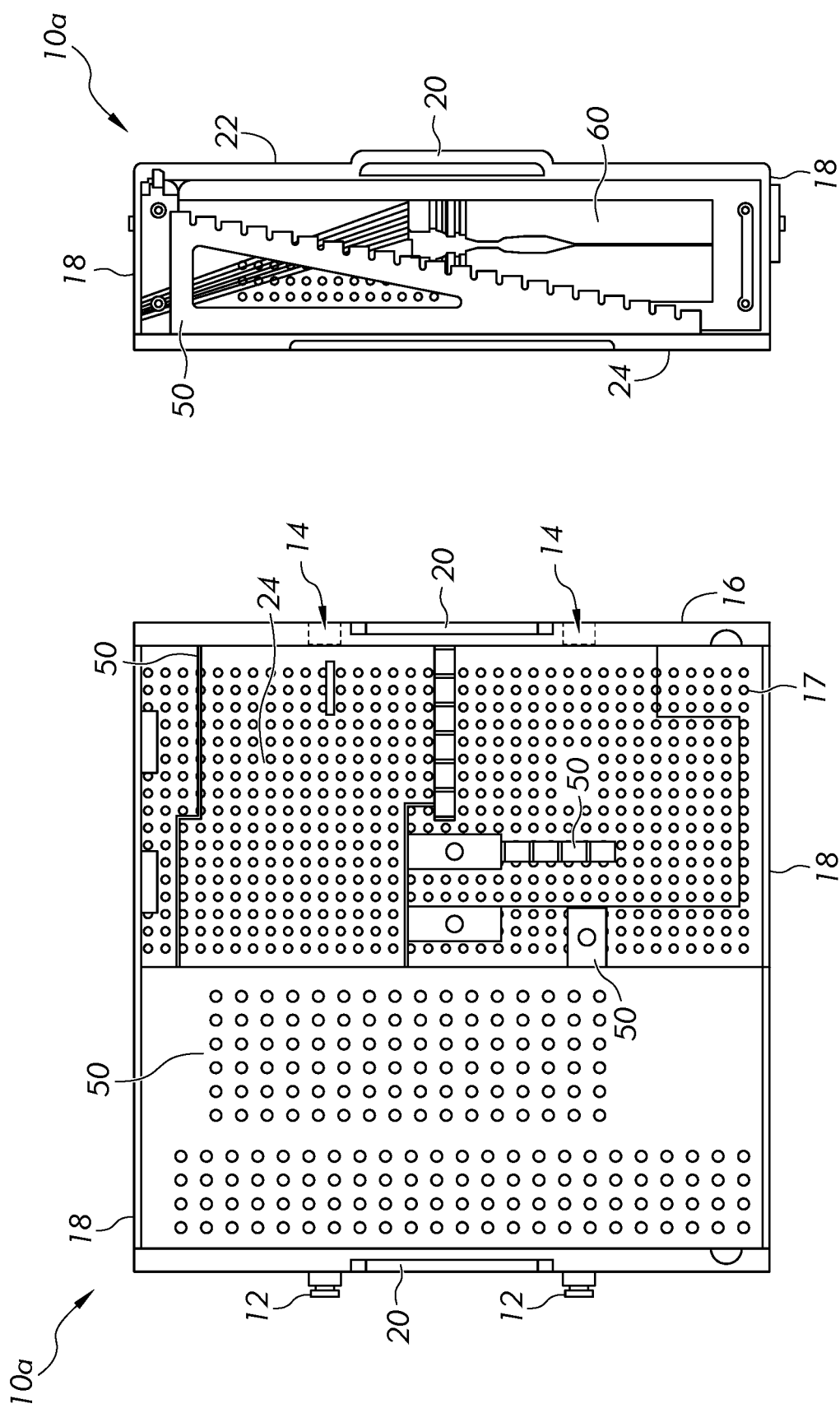
FIG. 4A depicts a top plan view of two illustrative component medical trays without lids and in a decoupled configuration according to one or more embodiments shown and described herein.

The at least one male mating feature 12 and the at least one female mating feature 14 are not limited by this disclosure, and may be any type of mating features. In some embodiments, the at least one male mating feature 12 and the at least one female mating feature 14 may incorporate one or more mechanical connections that allow selective fixation of the component medical trays 10a, 10b, 10c, 10d together via male/female coupling. For example, as depicted in FIGS. 1, 2, 4A, 4B, and 4C, the male mating feature 12 may be a peg or the like. As shown in FIGS. 3 and 4D, the at least one female mating feature 14 may be a recess that generally corresponds in shape and size to the male mating feature 12 such that the male mating feature 12 can be inserted therein. In some embodiments, the male mating feature 12 may include a notch or the like that allows the male mating feature 12 to be retained within the female mating feature 14.

In some embodiments, the component medical trays 10a, 10b, 10c, 10d may be selectively held together via an engagement mechanism 15, also referred to as a release mechanism. In some embodiments, the engagement mechanism 15 may be integrated with the at least one female mating feature 14 such that the engagement mechanism 15 releasably retains the at least one male mating feature 12 within the at least one female mating feature 14. Such an engagement mechanism 15 is not limited by this disclosure, and may generally be any engagement mechanism, such as, for example, a push to engage/push to disengage mechanism, a positive locking mechanism incorporated by the male mating feature 12 and/or a female mating feature 14, and/or the like. As described herein, the male mating feature 12 and the female mating feature 14 are not limited to the specific features shown herein, and may be comprised of nearly any feature that allows selective engagement and disengagement of the component medical trays 10a, 10b, 10c, 10d, such as fasteners, clamps, adhesive bonding, magnetic engagement, or other related selective engagement mechanisms.

Accordingly, the component medical trays 10a, 10b, 10c, 10d may be selectively engaged and disengaged from each other using the male mating feature 12 on a first one of the component medical trays 10a, 10b, 10c, 10d and the female mating feature 14 on a second one of the component medical trays 10a, 10b, 10c, 10d. More specifically, the male mating feature 12 on the first one of the component medical trays 10a, 10b, 10c, 10d may be inserted into the corresponding female mating feature 14 on the second one of the component medical trays 10a, 10b, 10c, 10d. In addition, the engagement mechanism 15 may activate such that the female mating feature 14 securely holds the male mating feature 12, thereby holding the first one of the component medical trays 10a, 10b, 10c, 10d to the second one of the component medical trays 10a, 10b, 10c, 10d. The first one of the component medical trays 10a, 10b, 10c, 10d can then be decoupled by deactivating the engagement mechanism 15 to release the male mating feature 12 from the female mating feature 14.

In various embodiments, each of the component medical trays 10a, 10b, 10c, 10d may include one or more handles 20 that may be used to facilitate carrying and transport of individual ones the component medical trays 10a, 10b, 10c, 10d and/or the adaptable medical tray 10. In some embodiments, the one or more handles 20 may be coupled to one or more of the side walls 16. In other embodiments, the one or more handles 20 may be integrated within one or more of the side walls 16. In some embodiments, the one or more handles may be located on the end walls 18, the top 22, and/or the bottom 24. In some embodiments, the handles 20 may be fixed to the side walls 16 such that the handles 20 are not movable. In some embodiments, the handles may be movable from an inset position to an extended position for use or may be otherwise connected to the component medical trays 10a, 10b, 10c, 10d to facilitate carrying of the component medical trays 10a, 10b, 10c, 10d and/or the adaptable medical tray 10. In other embodiments, the component medical trays 10a, 10b, 10c, 10d may not include the handles 20. Rather, the component medical trays 10a, 10b, 10c, 10d may include an external carrying strap, an external carrying mechanism, and/or a rolling carrier that carries one or more of the component medical trays 10a, 10b, 10c, 10d.

FIGS. 3-4D depict one component medical tray 10a. However, it should be understood that such a depiction is merely for illustrative purposes only, and is intended to encompass any of the component medical trays described herein. In some embodiments, various portions of a component medical tray 10a may include one or more passages 17 therethrough. The passages 17 may be located at any location on the component medical tray 10a. For example, the passages 17 may be located on one or more of the side walls 16 of the component medical tray 10a, one or more of the end walls 18, the top 22, and/or the bottom 24. The passages 17 may include holes, bores, or the like that extend through the side walls 16, the end walls, the top 22, and/or the bottom 24. In some embodiments, the passages 17 may be used for the insertion of screws, bolts, rivets, or the like 30 that are used to secure various components inside the component medical tray 10a, as described in greater detail herein. In some embodiments, the passages may be used to facilitate cleaning and sterilization of the various contents within the component medical tray 10a, such as by autoclaving or other cleaning or sterilization techniques.

Referring again to FIGS. 1-3, the component medical trays 10a, 10b, 10c, 10d may be constructed of a relatively strong and/or stiff structural material in some embodiments. In some embodiments, the component medical trays 10a, 10b, 10c, 10d may be constructed of one or more materials that may be subject to sterilization, cleaning, and/or sanitation processes and techniques, such as an autoclaving process. As such, the component medical trays 10a, 10b, 10c, 10d may be constructed of a sterilizable material. For example, the component medical trays 10a, 10b, 10c, 10d may be constructed of any metallic and/or any polymeric materials that are able to withstand the normal operating conditions of the component medical trays 10a, 10b, 10c, 10d, are able to engage and disengage with each other as described herein, are able to hold medical equipment therein, and/or have sufficient strength and stiffness to transport and store the various components. For example, the top 22 of the component medical trays 10a, 10b, 10c, 10d may be constructed of a polyphenylsulfone material, such as a Radel polymeric material. In another example, various portions of the component medical trays 10a, 10b, 10c, 10d, such as the one or more handles 20, portions of the end walls 18, and/or the like may be constructed of SAE 304 stainless steel. In another example, the bottom 24 and/or portions of the side walls 16 proximate the handles 20 may be constructed of 5052 aluminum. In another example, the at least one male mating feature 12 may be constructed of 17-4 stainless steel. In another example, the side walls 16 may be constructed of polypropylene, such as TecaPro heat stabilized polypropylene. In another example, various portions of the component medical trays 10a, 10b, 10c, 10d may be constructed of the same or similar materials as described hereinabove, particularly materials that that are able to withstand the normal operating conditions of the adaptable medical tray 10, such as Food and Drug Administration ("FDA") sterilization processes, and perform the various functions of the component medical trays 10a, 10b, 10c, 10d and/or the adaptable medical tray 10, as is described herein.

Figure 5A:
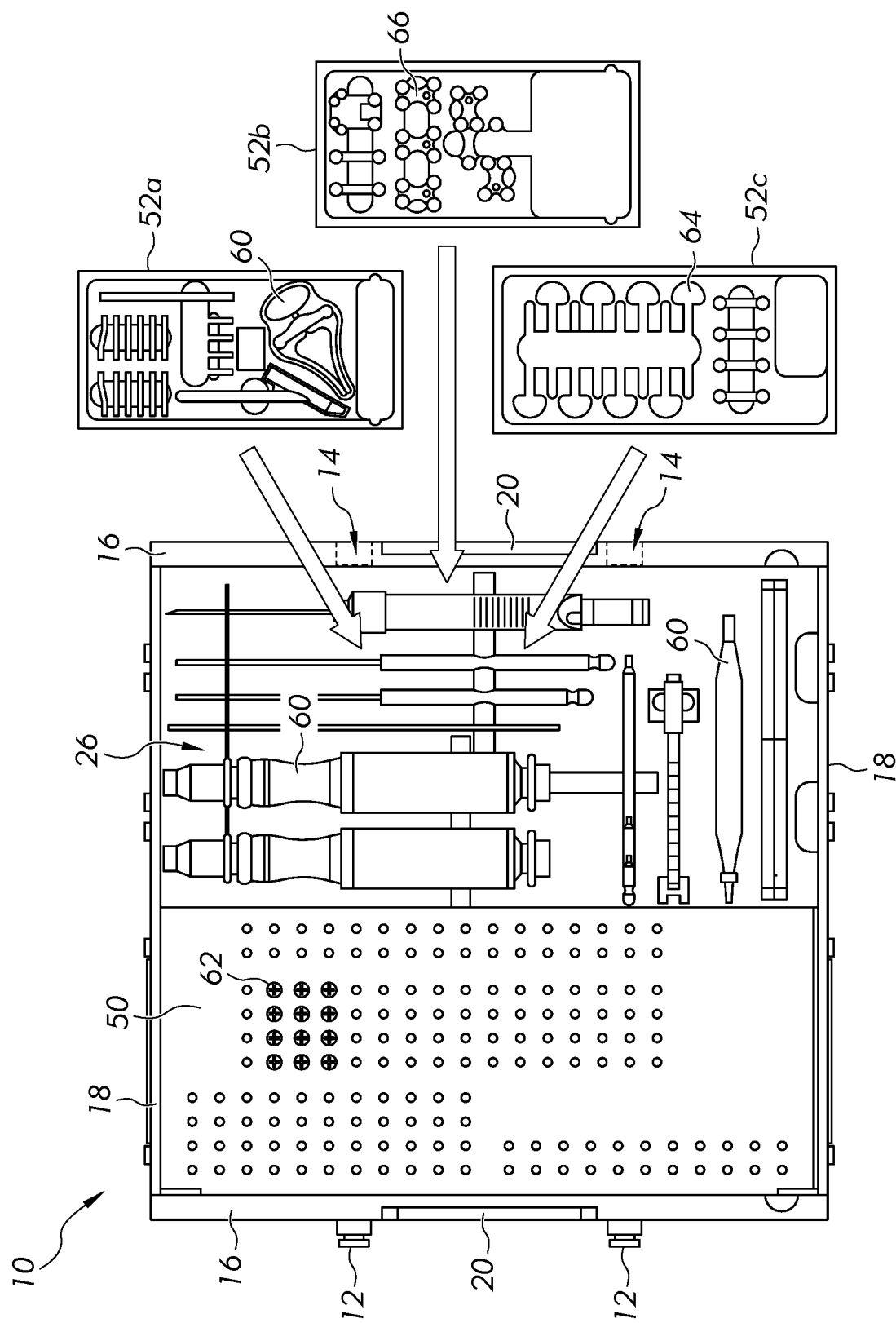
FIG. 5A depicts a top plan view of an illustrative component medical tray with removable tray inserts according to one or more embodiments shown and described herein.
Figure 5C:
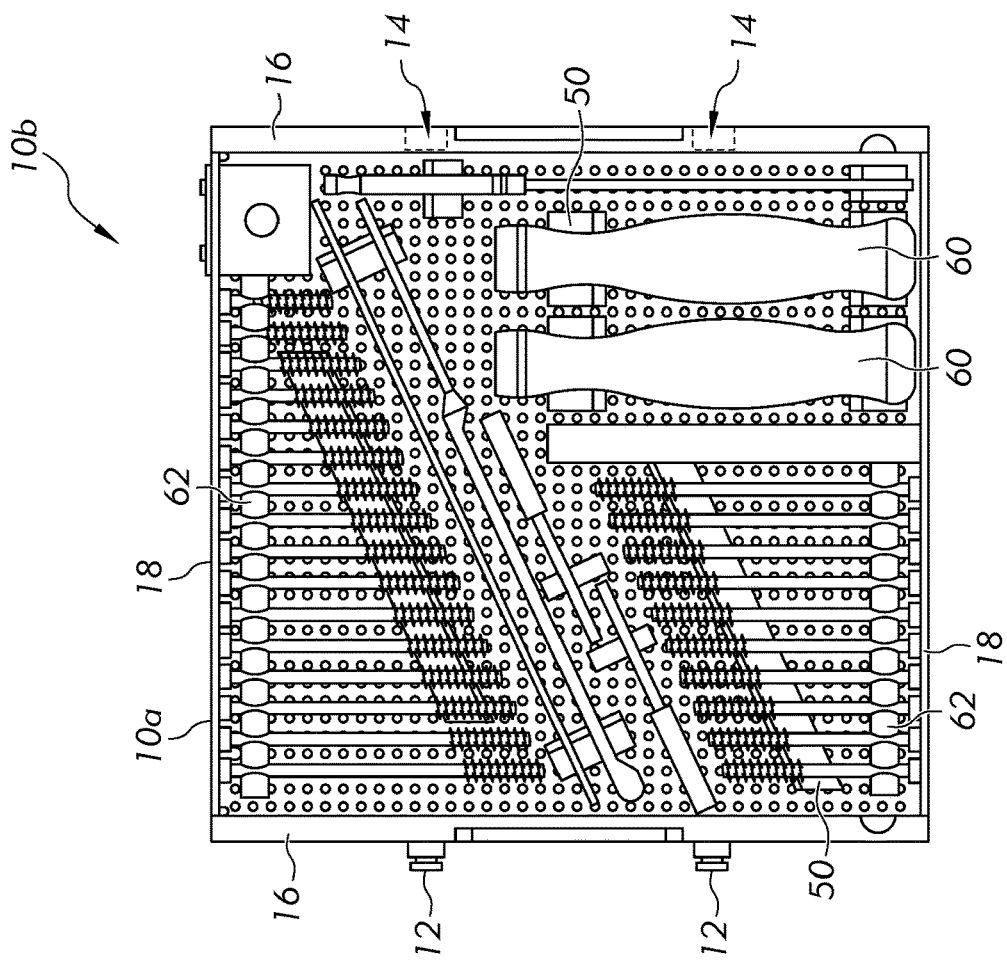
FIG. 5C depicts a top plan view of an illustrative component medical tray holding surgical screws and drivers according to one or more embodiments shown and described herein.
Figure 5B:
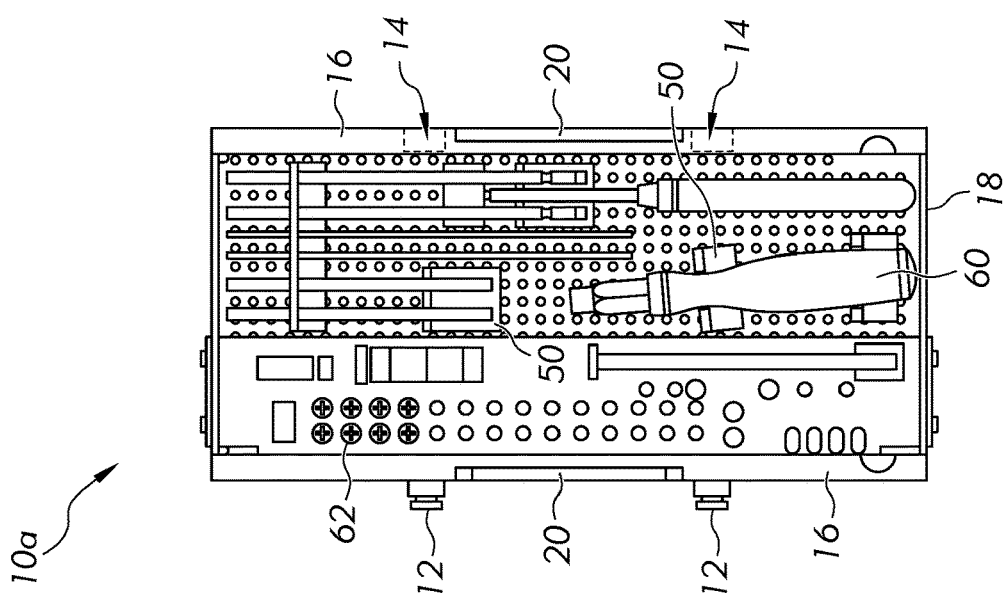
FIG. 5B depicts a top plan view of an illustrative component medical tray with device support inserts according to one or more embodiments shown and described herein.

Referring now to FIGS. 5A-13C, the component medical trays 10a, 10b, 10c, 10d, 10e, 10f, 10g may include various inserts that are designed to store and carry specific SKUs or SKU families, including implants, instruments, or other related medical equipment for a particular procedure. The various inserts contained within the component medical trays 10a, 10b, 10c, 10d, 10e, 10f, 10g are not limited by this disclosure, and may be any type of insert, particularly inserts that are generally understood as being used to retain, support, and/or organize various medical equipment. For example, an insert may be a support apparatus 50. In some embodiments, the support apparatus 50 may include a plurality of holes for which various screws 62 can be inserted, as shown in FIG. 5A. Such a support apparatus may include a plurality of steps that allow retention of screws having a particular length, as shown, for example, in FIG. 6A. In other embodiments, the support apparatus 50 may be a particularly sized and shaped tool retention device that retains one or more medical tools 60 in a held configuration, as shown, for example, in FIG. 5C.

In another example, as particularly shown in FIGS. 5A and 13A-13C, an insert may be a tray insert, such as a first tray insert 52a, a second tray insert 52b, and/or a third tray insert 52c, each of which holds particular types of medical equipment. The various tray inserts 52a, 52b, 52c may be particularly designed and/or configured for a specific positioning within the component medical trays 10a, 10b, 10c, 10d, 10e, 10f, 10g during use and/or to hold certain medical equipment. For example, the first tray insert 52a may hold medical tools 60, the second tray insert 52b may hold implants 66, and the third tray insert 52c may hold binders 64, such as suture materials, medical tape, staples, or the like. In some embodiments, one or more of the tray inserts 52a, 52b, 52c may be fixedly retained within the cavity 26 such that the tray inserts 52a, 52b, 52c cannot be removed. Such fixation may be achieved via bolts, screws, rivets, or the like that are inserted through the passages 17, as described in greater detail herein. In other embodiments, one or more of the tray inserts 52a, 52b, 52c may be removably retained within the cavity 26 such that the tray inserts 52a, 52b, 52c can be removed. For example, the various tray inserts 52a, 52b, 52c may be supported above certain medical equipment such that removal of the tray inserts 52a, 52b, 52c may be necessary to access the medical equipment. The removable tray inserts 52a, 52b, 52c may be removed, for example, by medical personnel prior to a procedure.

Figure 7:
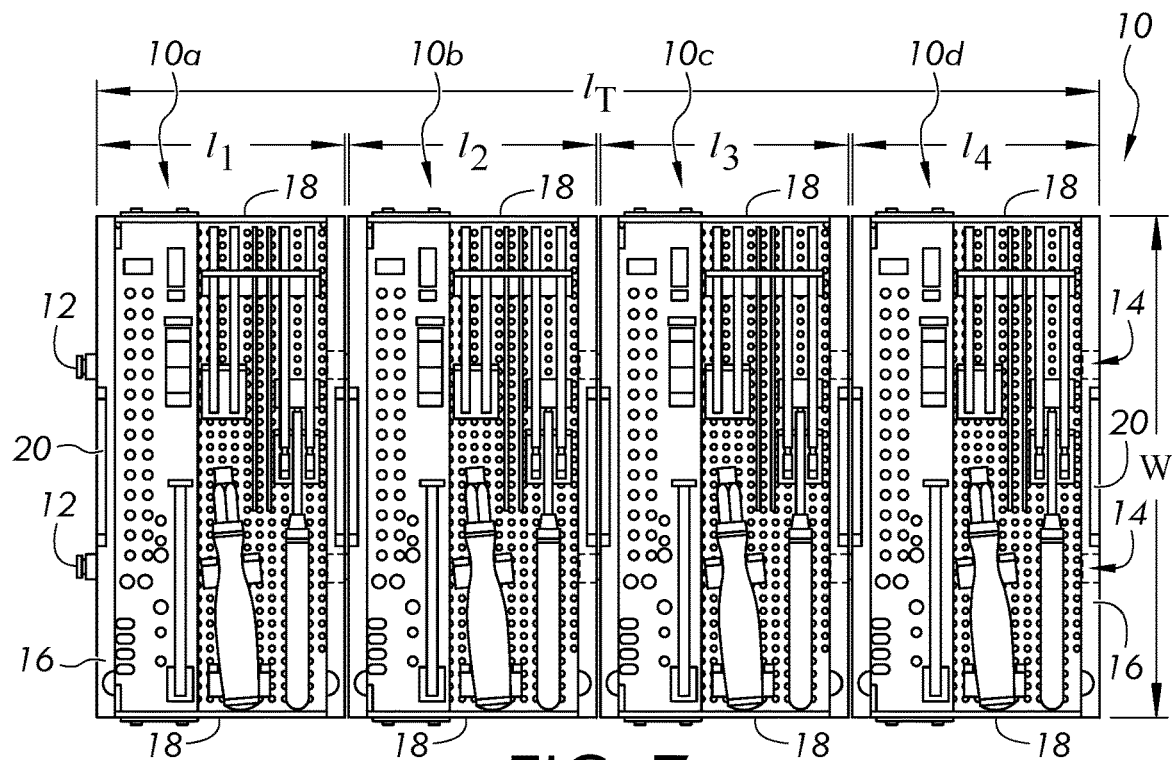
FIG. 7 depicts a top plan view of four illustrative component medical trays assembled in a coupled configuration to form an illustrative adaptable medical tray having a length to width ratio of 1:2 according to one or more embodiments shown and described herein.

The various component medical trays described herein may each have a particular size and/or shape. In some embodiments, the size and/or shape of a particular component medical tray may be a standard size and/or shape. In other embodiments, the size and/or shape of a particular component medical tray may be particularly configured for the medical equipment that it contains. That is, certain medical equipment may necessitate a larger component medical tray relative to other component medical trays to ensure that the medical equipment fits therein. In addition, the resulting adaptable medical tray 10 that is formed from the various component medical trays may vary in shape and/or size depending on the number of component medical trays that are coupled together and/or the size of each of the component medical trays. For example, as shown in FIG. 7, the adaptable medical tray 10 may include a first component medical tray 10a, a second component medical tray 10b, a third component medical tray 10c, and a fourth component medical tray 10d. Each of the component medical trays 10a, 10b, 10c, 10d may have a width w. In addition, the first component medical tray 10a may have a first length $l_1$, the second component medical tray 10b may have a second length $l_2$, the third component medical tray 10c may have a third length $l_3$, and the fourth component medical tray 10d may have a fourth length $l_4$. In some embodiments, the first length $l_1$, the second length $l_2$, the third length $l_3$, and the fourth length $l_4$ may be substantially equal. When the component medical trays 10a, 10b, 10c, 10d are coupled together to form the adaptable medical tray 10, the adaptable medical tray 10 may have the same width w and a total length $l_T$ that equals a sum of the first length $l_1$, the second length $l_2$, the third length $l_3$, and the fourth length $l_4$. It should be understood that because each of the component medical trays 10a, 10b, 10c, 10d can stand alone on their own (i.e., they each have their own respective components and do not share components such as a lid or a configuration tray), the component medical trays 10a, 10b, 10c, 10d can thus be coupled together in any configuration without the need to conform to particular shapes and/or sizes that would be dictated by shared components such as shared lids or configuration trays.

Figure 8:
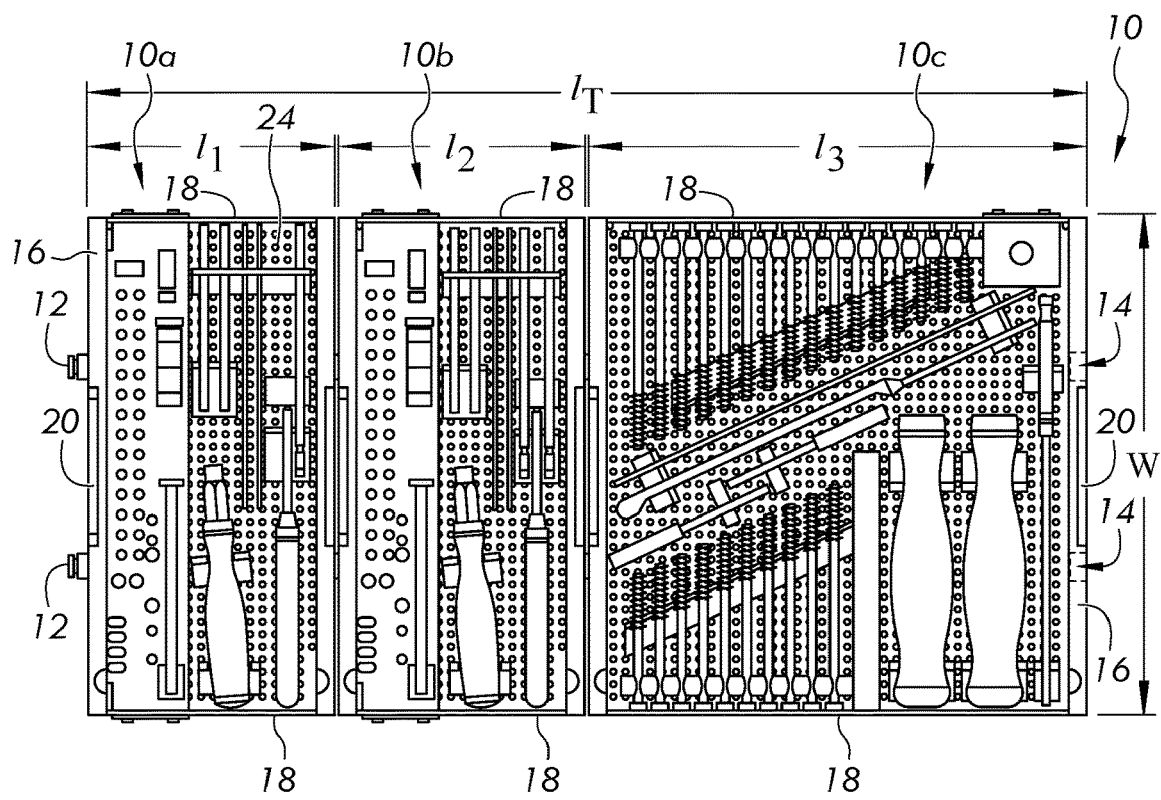
FIG. 8 depicts a top plan view of three illustrative component medical trays assembled in a coupled configuration to form another illustrative adaptable medical tray having a length to width ratio of 1:2 according to one or more embodiments shown and described herein.
Figure 10:
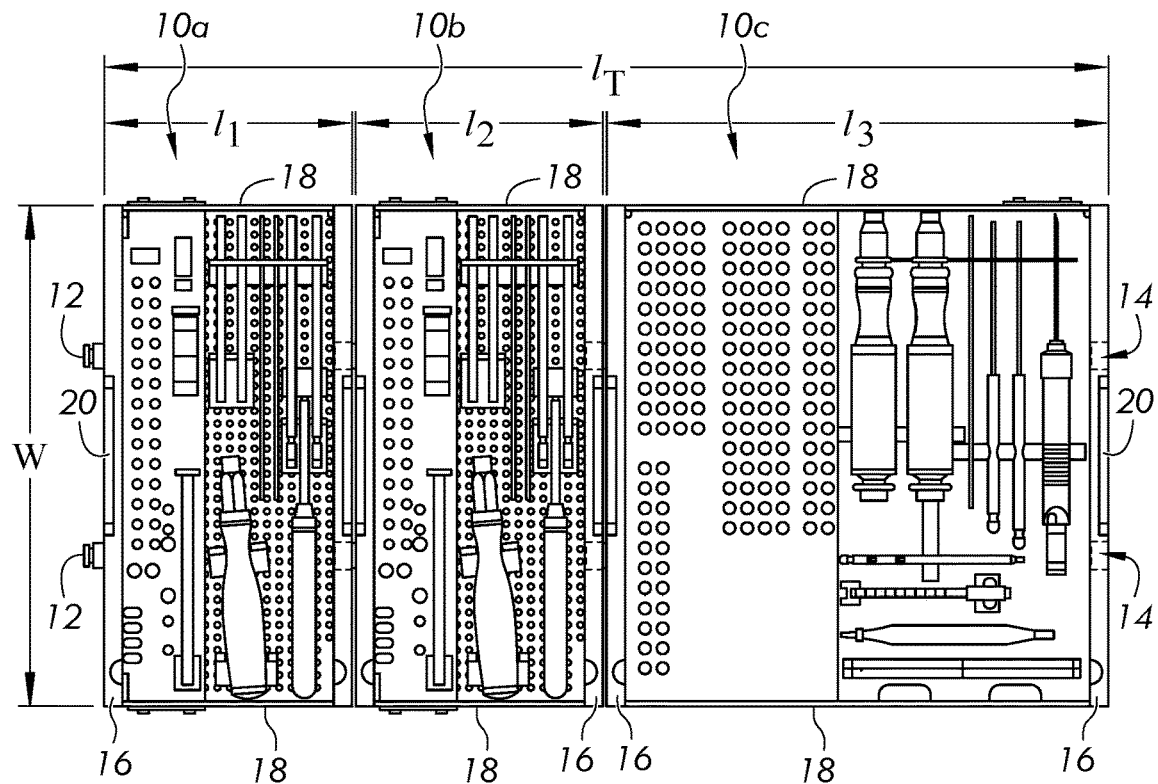
FIG. 10 depicts a top plan view of three illustrative component medical trays assembled in a coupled configuration to form yet another illustrative 10×20 adaptable medical tray according to one or more embodiments shown and described herein.

As shown in FIGS. 8 and 10, the adaptable medical tray 10 may include a first component medical tray 10a, a second component medical tray 10b, and a third component medical tray 10c, where the first component medical tray 10a has a first length $l_2$, the second component medical tray 10b has a second length $l_2$, and the third component medical tray 10c has a third length $l_3$. The first length $l_1$ and the second length $l_2$ are equal to one another, and the third length $l_3$. is equal to the combined first length $l_1$ and second length $l_2$. Each of the first component medical tray 10a, the second component medical tray 10b, and the third component medical tray 10c may have a width w. When the component medical trays 10a, 10b, 10c are coupled together to form the adaptable medical tray 10, the adaptable medical tray 10 may have the same width w and a total length $l_T$ that equals a sum of the first length $l_1$, the second length $l_2$, and the third length $l_3$.

Figure 9:
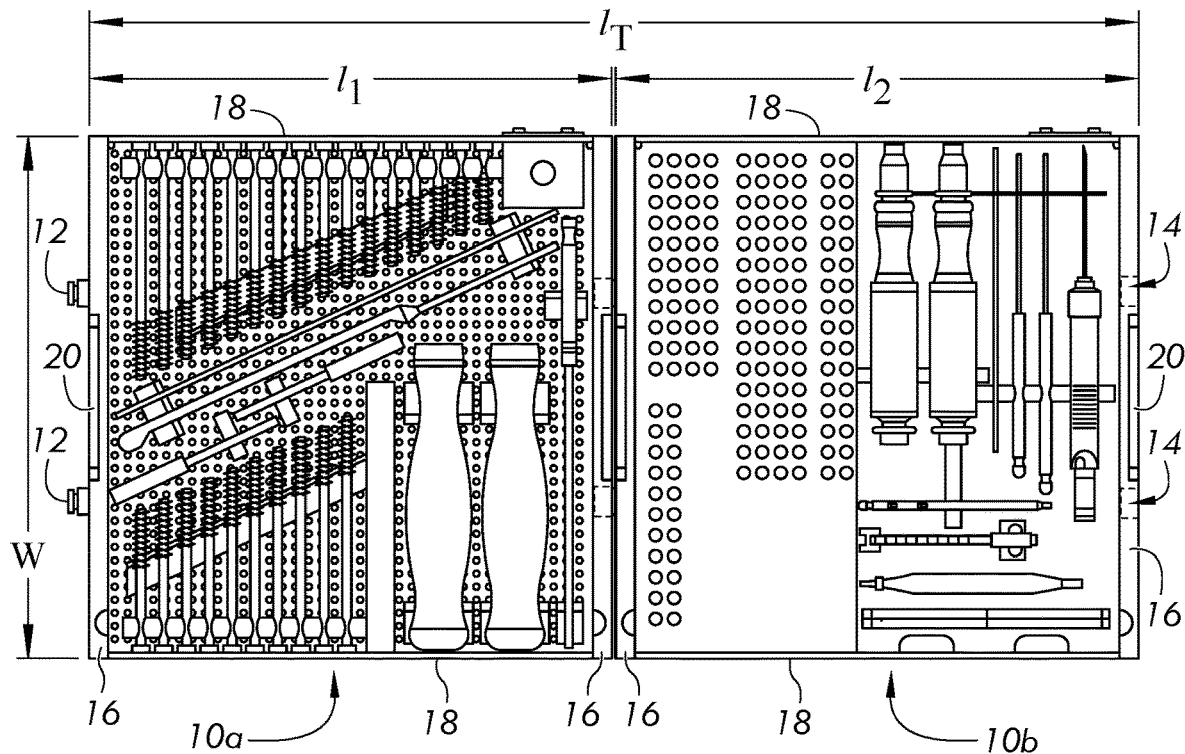
FIG. 9 depicts a top plan view of two illustrative component medical trays assembled in a coupled configuration to form yet another illustrative adaptable medical tray having a length to width ratio according to one or more embodiments shown and described herein.

As shown in FIG. 9, the adaptable medical tray 10 may include a first component medical tray 10a and a second component medical tray 10b, where the first component medical tray 10a has a first length $l_1$ and the second component medical tray 10b has a second length $l_2$. The first length $l_1$ and the second length $l_2$ are equal to one another. Each of the first component medical tray 10a and the second component medical tray 10b may have a width w. When the component medical trays 10a, 10b are coupled together to form the adaptable medical tray 10, the adaptable medical tray 10 may have the same width w and a total length $l_T$ that equals a sum of the first length $l_1$ and the second length $l_2$.

In operation, a user may determine a particular set of SKUs or SKU families that are required for a particular medical procedure, based on the user's experience, recommendation of a medical professional, a particular medical guideline, and/or the like. Only the medical equipment, including implants, instruments and related components may be selected based on their inclusion in the component medical trays 10a, 10b, 10c, 10d, 10e, 10f, 10g and the user may couple the correct or selected component medical trays 10a, 10b, 10c, 10d, 10e, 10f, 10g for the procedure. Additional SKUs or SKU families may be added to the component medical trays 10a, 10b, 10c, 10d, 10e, 10f, 10g by inserting appropriate inserts 52a, 52b, 52c that may be required for the procedure. The coupled component medical trays 10a, 10b, 10c, 10d, 10e, 10f, 10g are transported to the medical procedure, the appropriate implants, instruments and related components from the adaptable medical tray 10 is utilized during the procedure and the adaptable medical tray 10 with the remaining components therein may be sterilized following the procedure. The user is then able to return the adaptable medical tray 10 to inventory and disassemble the component medical trays 10a, 10b, 10c, 10d, 10e, 10f, 10g for subsequent use after replacing used implants or related components.

It should now be understood that the plurality of component medical trays described herein can be coupled to one another in any number of configurations to form an adaptable medical tray that contains specific medical equipment that is selected for a particular procedure, according to a particular medical personnel's preferences, according to guidelines, and/or the like. Moreover, the adaptable medical tray can be split into its component medical trays after sterilization without the need to remove the respective tops from the component medical trays such that the component medical trays can be transported to different locations, can be swapped out, and/or the like. Even more, the adaptable medical tray can be coupled from its constituent parts or split into its constituent parts without the need for external joining devices or tools.

Certain terminology is used herein for convenience only and is not limiting. Unless specifically set forth herein, the terms "a", "an" and "the" are not limited to one element but instead should be read as meaning "at least one". The words "right," "left," "lower," and "upper" designate directions in the drawings to which reference is made. The words "inwardly" or "distally" and "outwardly" or "proximally" refer to directions toward and away from, respectively, the geometric center or orientation of the device and instruments and related parts thereof. The words, "anterior", "posterior", "superior", "inferior", "lateral" and related words and/or phrases designate preferred positions, directions and/or orientations in the human body to which reference is made and are not meant to be limiting. The terminology includes the above listed words, derivatives thereof and words of similar import.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. An adaptable medical tray comprising:
a first component medical tray comprising: a first plurality of walls, a first bottom, and a first removable top, the first plurality of walls and the first bottom arranged to form a first cavity in the first component medical tray, at least two opposing walls of the first plurality of walls having a first length, at least one of the first plurality of walls, the first bottom, and the first removable top comprising one or more passages therethrough that facilitate sterilization of contents within the first cavity; and
a second component medical tray removably coupled to the first component medical tray, wherein the second component medical tray comprises a second plurality of walls, a second bottom, and a second removable top, the second plurality of walls and the second bottom arranged to form a second cavity in the second component medical tray, at least two opposing walls of the second plurality of walls having a second length that is different from the first length,
wherein:
the first component medical tray and the second component medical tray are constructed of a sterilizable material,
the first component medical tray is decouplable from the second component medical tray after a sterilization process without removing the first removable top from the first cavity and without removing the second removable top from the second cavity;
each of the first component medical tray and the second component medical tray couple to one another along a common interface via one or more mating features positioned along the common interface;
the first component medical tray comprises a release mechanism positioned along a wall adjacent to the common interface and spaced from the common interface,
the one or more mating features comprise a female mating feature arranged on the first component medical tray and a corresponding male mating feature arranged on the second component medical tray and the release mechanism pushable along an axis perpendicular to an axis of the female mating feature, actuates the female mating feature to engage and disengage the female mating feature with the male mating feature of the second component medical tray.

2. The adaptable medical tray of claim 1, further comprising a third component medical tray removably coupled to the first component medical tray or the second component medical tray, the third component medical tray comprising a third plurality of walls, a third bottom, and a third removable top, wherein the third plurality of walls and the third bottom are arranged to form a third cavity in the third component medical tray.

3. The adaptable medical tray of claim 1, wherein at least one of the first plurality of walls comprises at least one first retention piece and at least one of the second plurality of walls comprises at least one second retention piece, the at least one first retention piece corresponding to the at least one second retention piece to allow the first component medical tray to be removably coupled to the second component medical tray.

4. The adaptable medical tray of claim 3, wherein the at least one first retention piece comprises at least one male mating feature and the at least one second retention piece comprises at least one female mating feature.

5. The adaptable medical tray of claim 1, further comprising a tray insert retained within the first cavity.

6. The adaptable medical tray of claim 5, wherein the tray insert is fixedly retained within the first cavity.

7. The adaptable medical tray of claim 5, wherein the tray insert is removably retained within the first cavity.

8. The adaptable medical tray of claim 1, further comprising one or more tray inserts retained within the first cavity and one or more tray inserts retained within the second cavity.

9. The adaptable medical tray of claim 1, further comprising one or more tool retention devices for holding a medical tool within the first cavity.

10. The adaptable medical tray of claim 9, further comprising the medical tool held by at least one of the one or more first tool retention devices.

11. The adaptable medical tray of claim 1, further comprising one or more first tool retention devices for holding a first medical tool within the first cavity and one or more second tool retention devices for holding a second medical tool within the second cavity.

12. The adaptable medical tray of claim 1, wherein:
the first cavity retains a first SKU and the second cavity retains a second SKU; or
the first cavity and the second cavity each retain a set of SKUs.

13. An adaptable medical tray comprising:
a first component medical tray comprising a first plurality of side walls, a first plurality of end walls, a first bottom, and a first removable top, the first plurality of side walls, the first plurality of end walls, and the first bottom arranged to form a first cavity in the first component medical tray, at least one of the first plurality of side walls comprising at least one male mating feature, and at least one of the first plurality of walls, the first bottom, and the first removable top comprising one or more passages therethrough that facilitate sterilization of contents within the first cavity; and
a second component medical tray comprising a second plurality of side walls, a second plurality of end walls, a second bottom, and a second removable top, the second plurality of side walls, the second plurality of end walls, and the second bottom arranged to form a second cavity in the second component medical tray, at least one of the second plurality of side walls comprising at least one female mating feature that corresponds to the at least one male mating feature, wherein:
when the at least one male mating feature is inserted in the at least one female mating feature, the first component medical tray is removably coupled to the second component medical tray in a side-by-side configuration along a common interface,
the first component medical tray and the second component medical tray are constructed of a sterilizable material, and
the first component medical tray is decouplable from the second component medical tray after a sterilization process without removing the first removable top from the first cavity and without removing the second removable top from the second cavity;
the first component medical tray comprises a release mechanism positioned along a wall adjacent to the common interface and spaced from the common interface, and
the release mechanism, pushable along an axis perpendicular to an axis of the at least one female mating feature, actuates the at least one female mating feature to engage and disengage the at least one female mating feature with the at least one male mating feature of the first component medical tray;
opposing sidewalls of the first component medical tray and the second component medical tray define slots for receiving the first removable top and the second removable top, respectively, and allowing the first removable top and the second removable top to slide along a length of the opposing sidewalls of the first component medical tray and the second component medical tray within the slots.

14. The adaptable medical tray of claim 13, further comprising a third component medical tray removably coupled to the first component medical tray or the second component medical tray, the third component medical tray comprising a third plurality of side walls, a third plurality of end walls, a third bottom, and a third removable top, wherein the third plurality of side walls, the third plurality of end walls, and the third bottom are arranged to form a third cavity in the third component medical tray.

15. The adaptable medical tray of claim 13, wherein:
a first side wall of the first plurality of side walls comprises a plurality of male mating features and a second side wall of the first plurality of side walls comprises a plurality of female mating features;
a first side wall of the second plurality of side walls comprises a plurality of male mating features and a second side wall of the second plurality of side walls comprises a plurality of female mating features such that the first component medical tray is couplable to the second component medical tray in a plurality of configurations.

16. The adaptable medical tray of claim 13, wherein:
the first cavity holds at least a portion of a first SKU or at least a portion of a first SKU family; and
the second cavity holds at least a portion of a second SKU or at least a portion of a second SKU family.

17. The adaptable medical tray of claim 13, wherein the first cavity holds a first portion of a SKU and the second cavity holds a second portion of a SKU.

18. The adaptable medical tray of claim 13, wherein each of the first cavity and the second cavity holds at least a portion of a SKU or at least a portion of a SKU family.

19. An adaptable medical tray comprising:
a first component medical tray constructed of a sterilizable material and comprising a cavity formed by:
a first side wall comprising a plurality of male mating features,
a second side wall comprising a plurality of female mating features,
a plurality of end walls,
a bottom, and
a removable top,
at least one of the first side wall, the second side wall, the plurality of end walls, the bottom, and the removable top comprising one or more passages therethrough that facilitate sterilization of contents within the cavity; and
a release mechanism coupled to the plurality of female mating features and engagement by a user at one of the plurality of end walls and spaced from a surface of the second side wall;
a second component medical tray constructed of a sterilizable material and comprising a cavity formed by:
a first side wall comprising a plurality of male mating features,
a second side wall comprising a plurality of female mating features,
a plurality of end walls,
a bottom, and
a removable top; and
a third component medical tray constructed of a sterilizable material and comprising a cavity formed by:
a first side wall comprising a plurality of male mating features,
a second side wall comprising a plurality of female mating features,
a plurality of end walls,
a bottom, and
a removable top;
wherein:
the first component medical tray is removably coupled to the second component medical tray and the third component medical tray in a side-by-side configuration via the plurality of male mating features of the first side wall of the first component tray and the plurality of female mating features of the second side wall of the first component tray, and
the first component medical tray is decouplable from the second component medical tray and the third component medical tray after a sterilization process without removing the removable top from the first cavity, the removable top from the second cavity, and the removable top from the third cavity;
the release mechanism, pushable along an axis perpendicular to an axis of the plurality of female mating features, actuates the plurality of female mating features to engage and disengage the plurality of female mating features with the plurality of male mating features of the second component medical tray.

20. The adaptable medical tray of claim 19, wherein the release mechanism comprises a push to engage and push to disengage mechanism.

* * * * *